United States Patent [19]

Kriesel et al.

[11] Patent Number: 5,531,683
[45] Date of Patent: Jul. 2, 1996

[54] MIXING AND DELIVERY SYRINGE ASSEMBLY

[75] Inventors: Marshall S. Kriesel, St. Paul; Thomas N. Thompson, Richfield, both of Minn.

[73] Assignee: Science Incorporated, Bloomington, Minn.

[21] Appl. No.: 271,378

[22] Filed: Jul. 6, 1994

Related U.S. Application Data

[63] Continuation-in-part of Ser. No. 930,749, Aug. 13, 1992, Pat. No. 5,330,426.

[51] Int. Cl.⁶ .................................................. A61M 37/00
[52] U.S. Cl. ................... 604/89; 604/82; 604/88; 604/416
[58] Field of Search ..................... 604/82–93, 148, 604/139, 890.1, 200–205, 226, 411–416, 221–222, 231–232, 235, 244–246

[56] References Cited

U.S. PATENT DOCUMENTS

| | | | |
|---|---|---|---|
| 4,606,734 | 8/1986 | Larkin et al. | 604/84 |
| 4,681,582 | 7/1987 | Yamamoto | 604/890.1 |
| 4,871,360 | 10/1989 | Theeuwes | 604/892.1 |
| 4,985,017 | 1/1991 | Theeuwes | 604/92 |
| 5,137,511 | 8/1992 | Reynolds | 604/88 |
| 5,286,257 | 2/1994 | Fischer | 604/82 |
| 5,336,192 | 8/1994 | Palestrant | 604/167 |
| 5,397,303 | 3/1995 | Sancoff et al. | 604/82 |

*Primary Examiner*—C. Fred Rosenbaum
*Assistant Examiner*—V. Alexander
*Attorney, Agent, or Firm*—J. E. Brunton

[57] ABSTRACT

A device for intermixing a first component, such as a parenteral fluid with a second component, such as an immobilized drug carried by a scaffold to form a beneficial agent which, following the mixing step, can be dispensed directly from the device for infusion into a patient. The device includes novel mechanisms for mateably interconnecting a container, such as a glass vial containing the first component with a housing having a fluid outlet which houses a sealed container containing the second component, and then for controllably mixing the components under sterile conditions to form an injectable solution which is automatically dispensed through the fluid outlet of the device.

38 Claims, 12 Drawing Sheets

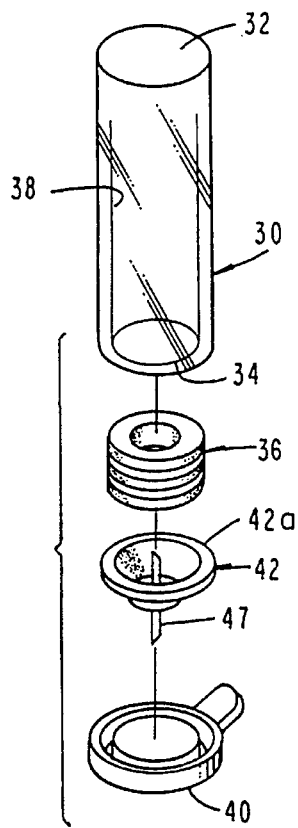
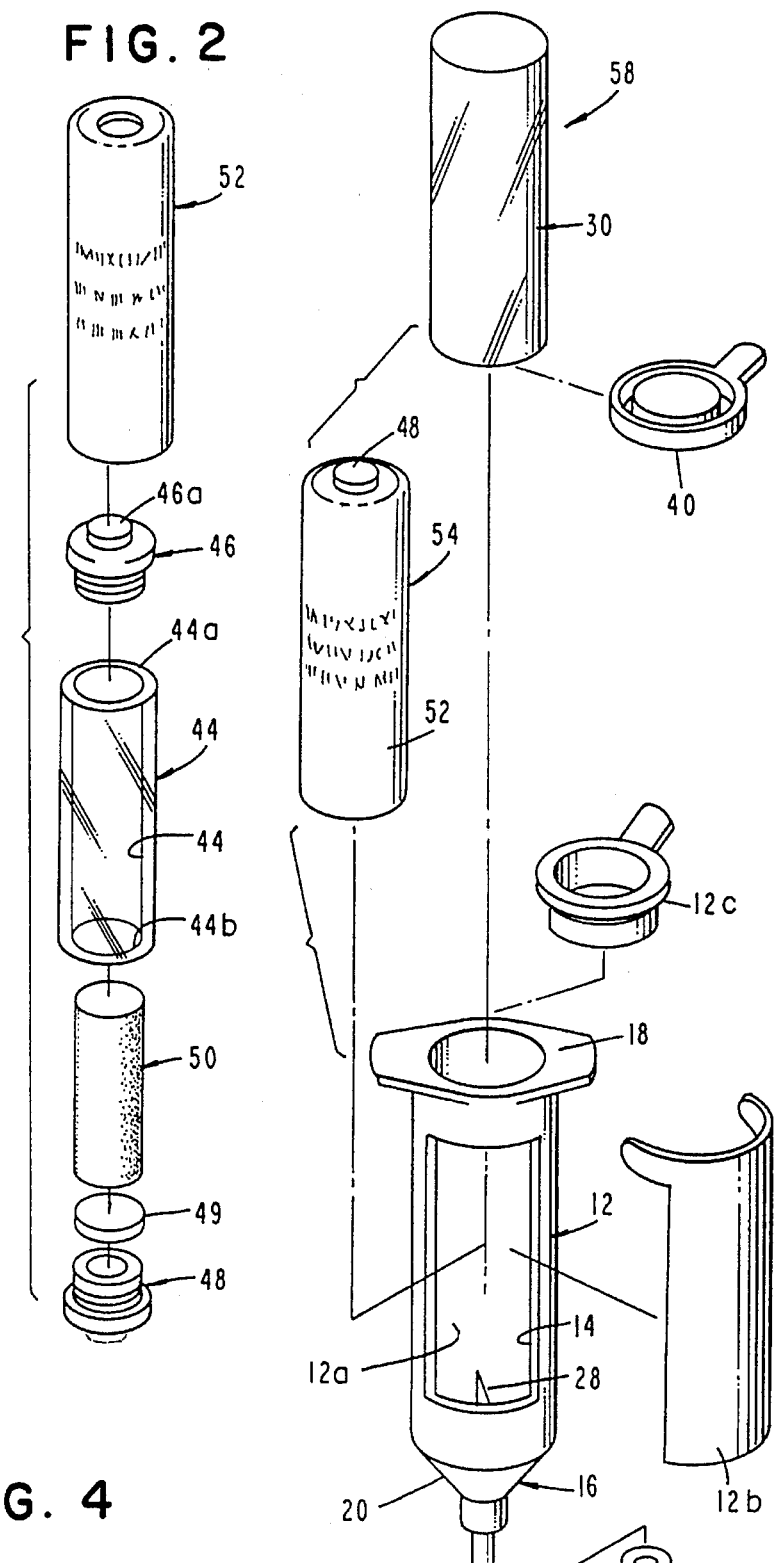
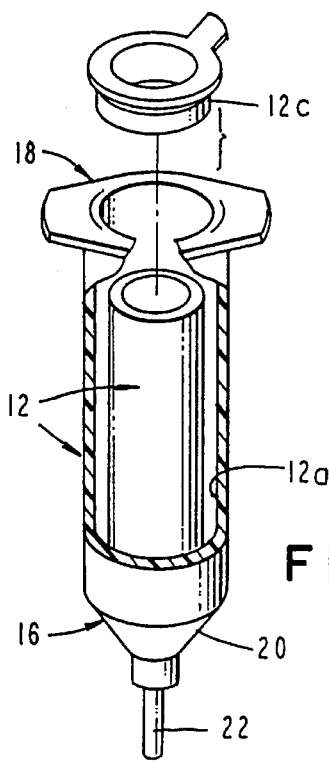
FIG. 1
FIG. 2
FIG. 3
FIG. 4

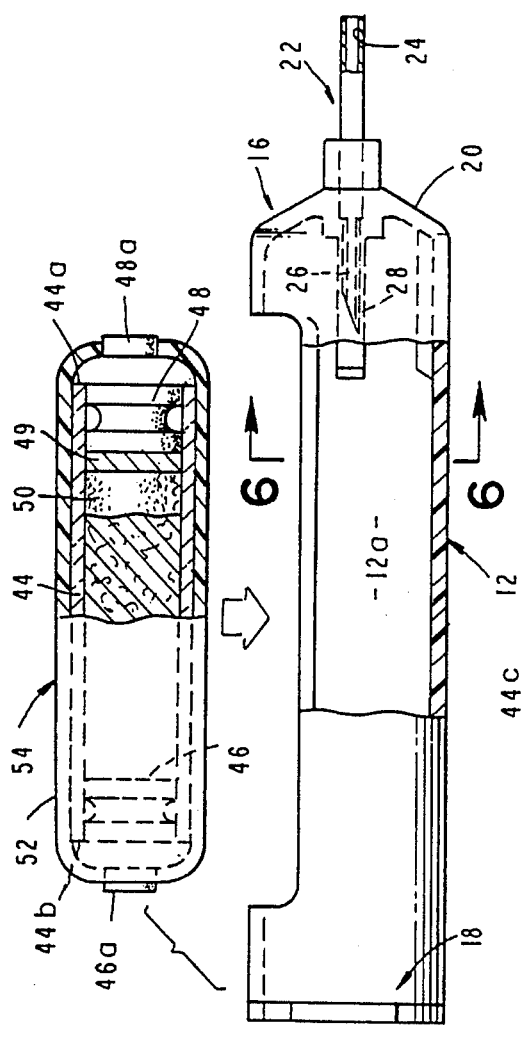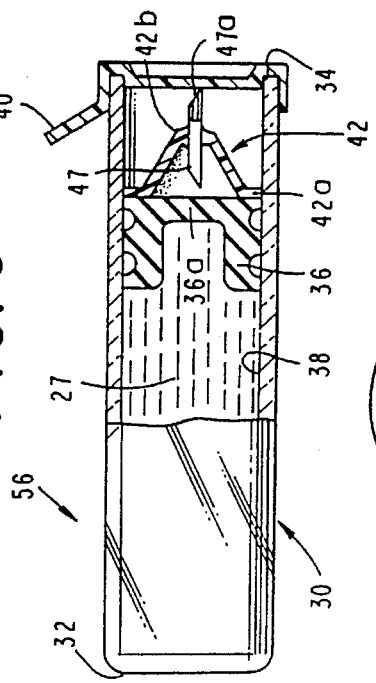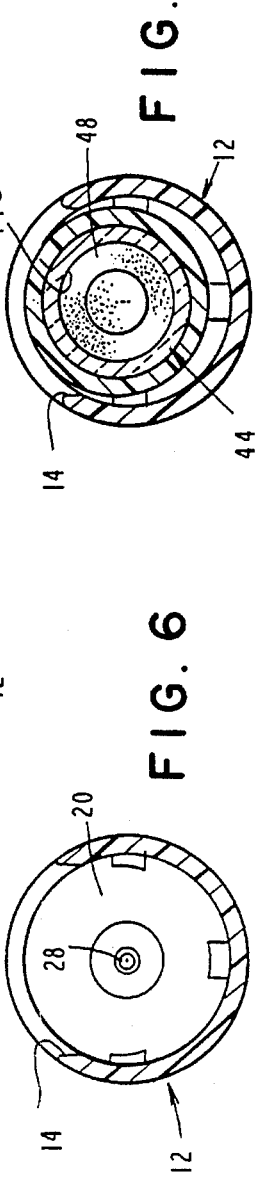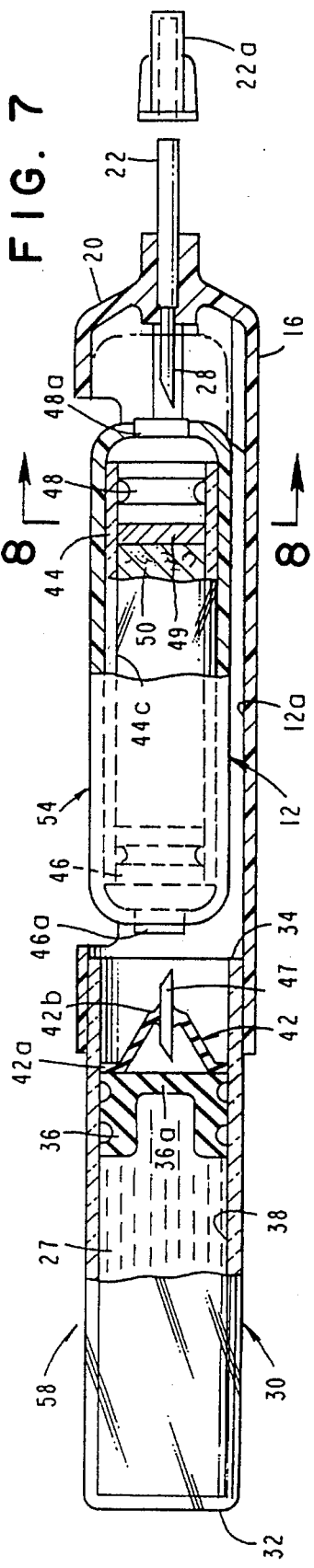

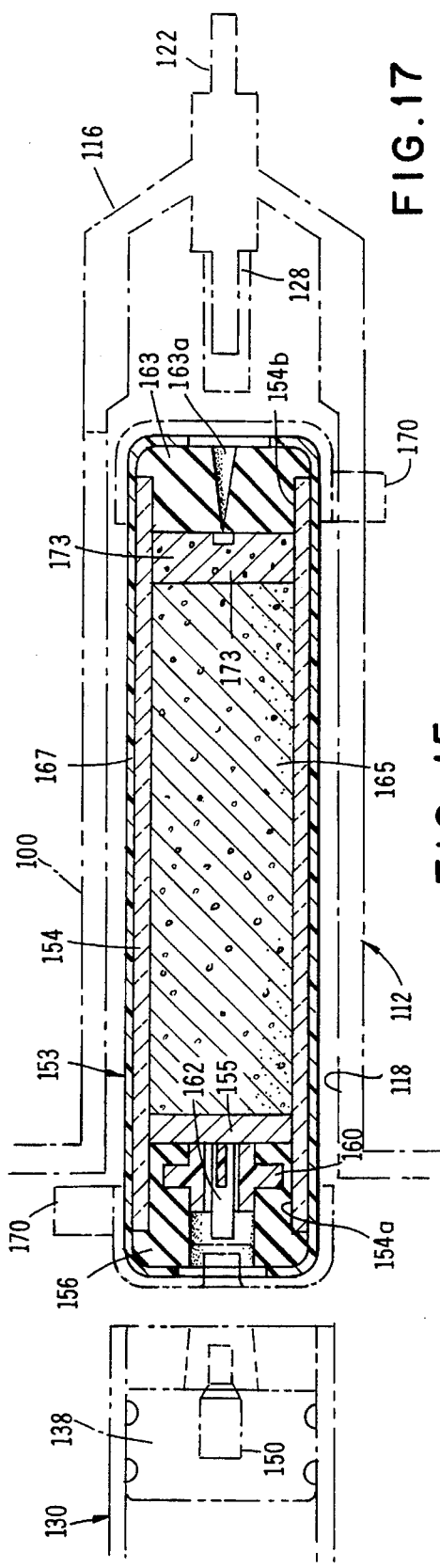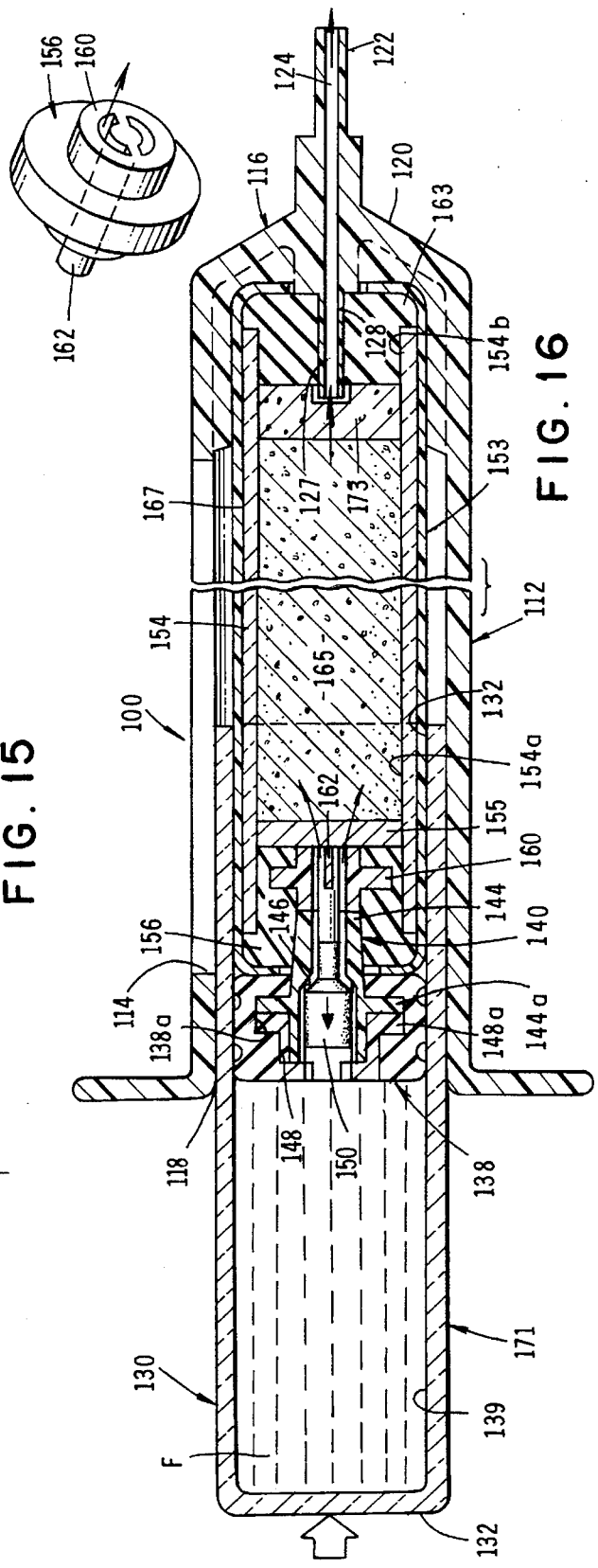

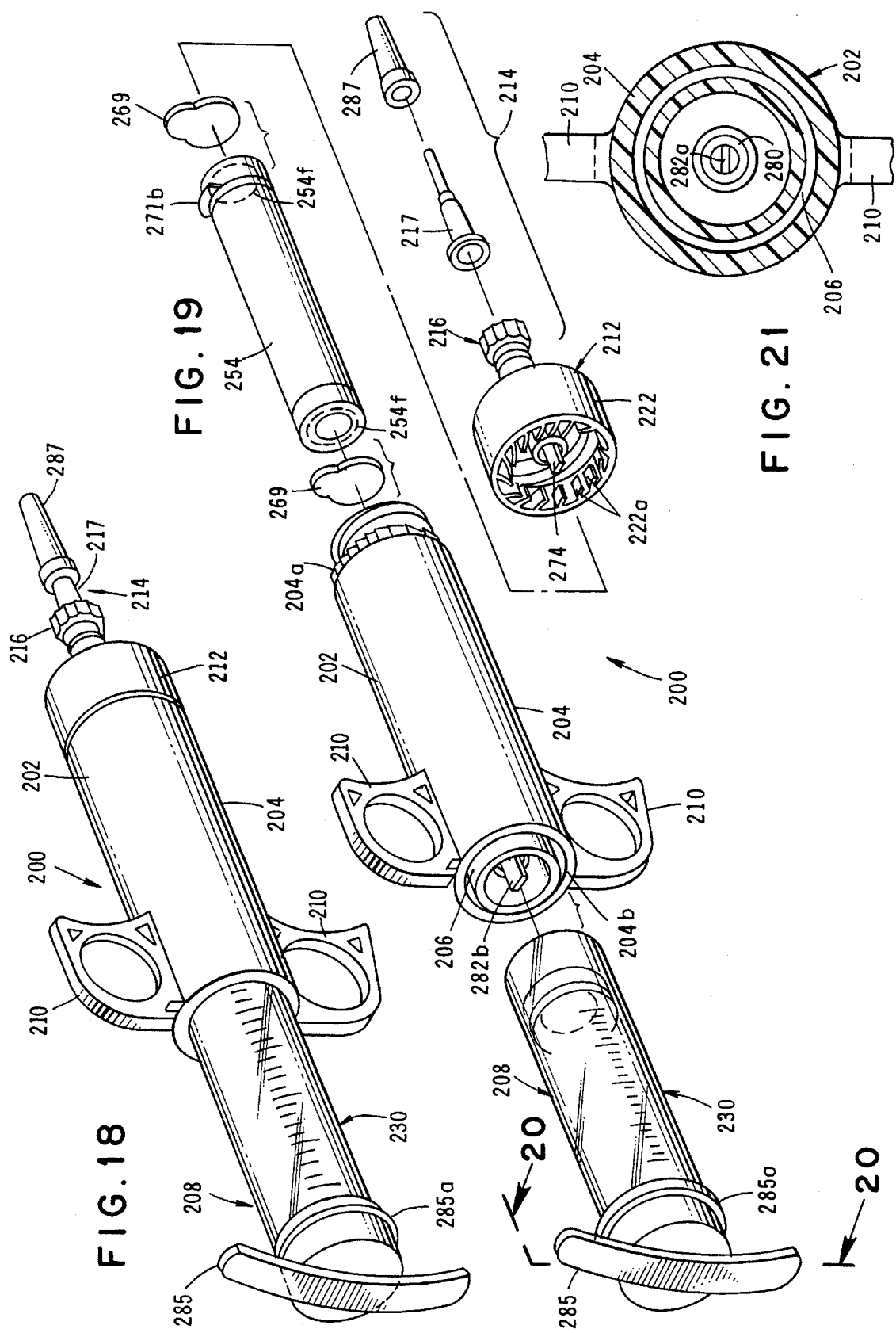

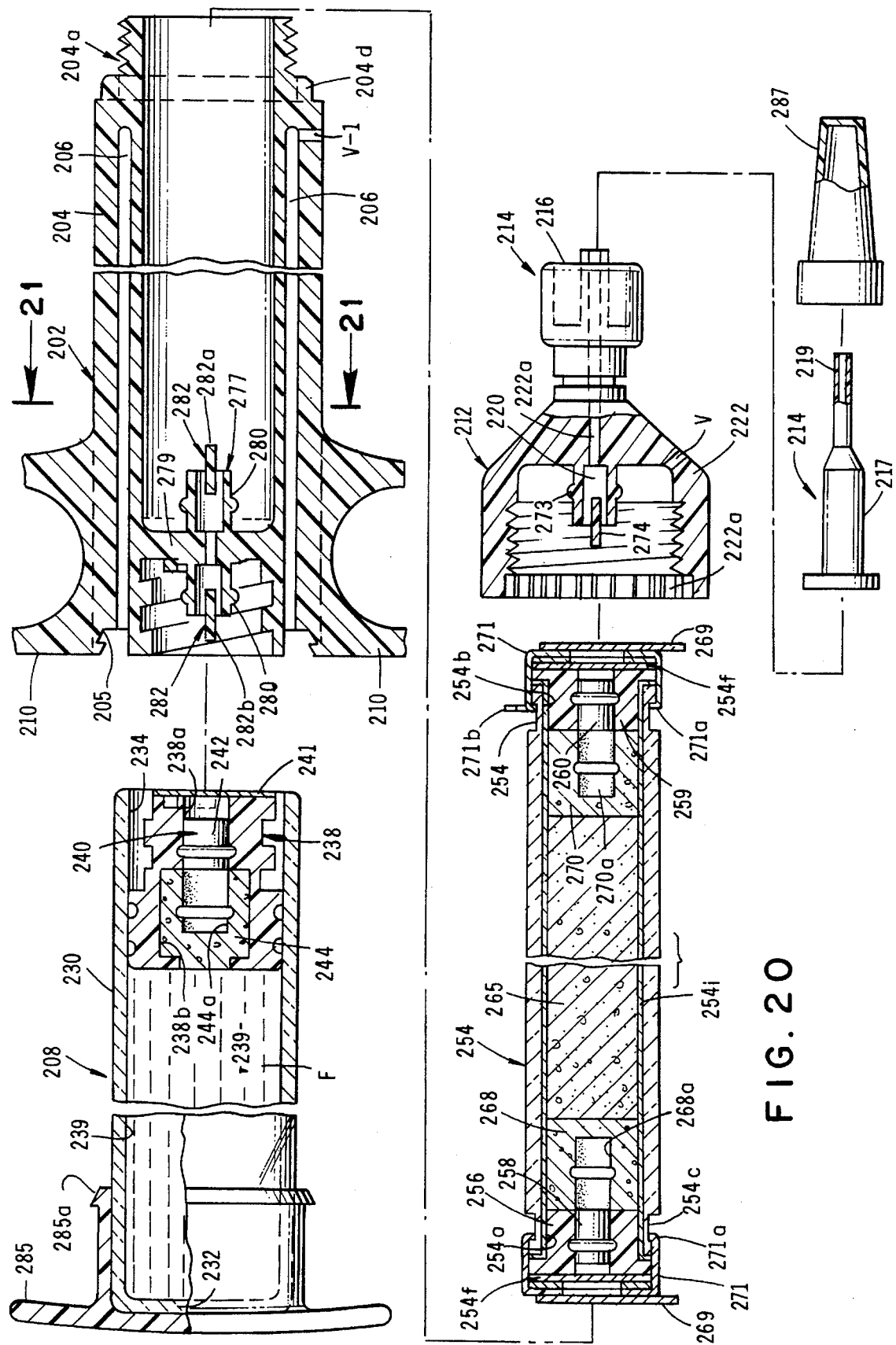

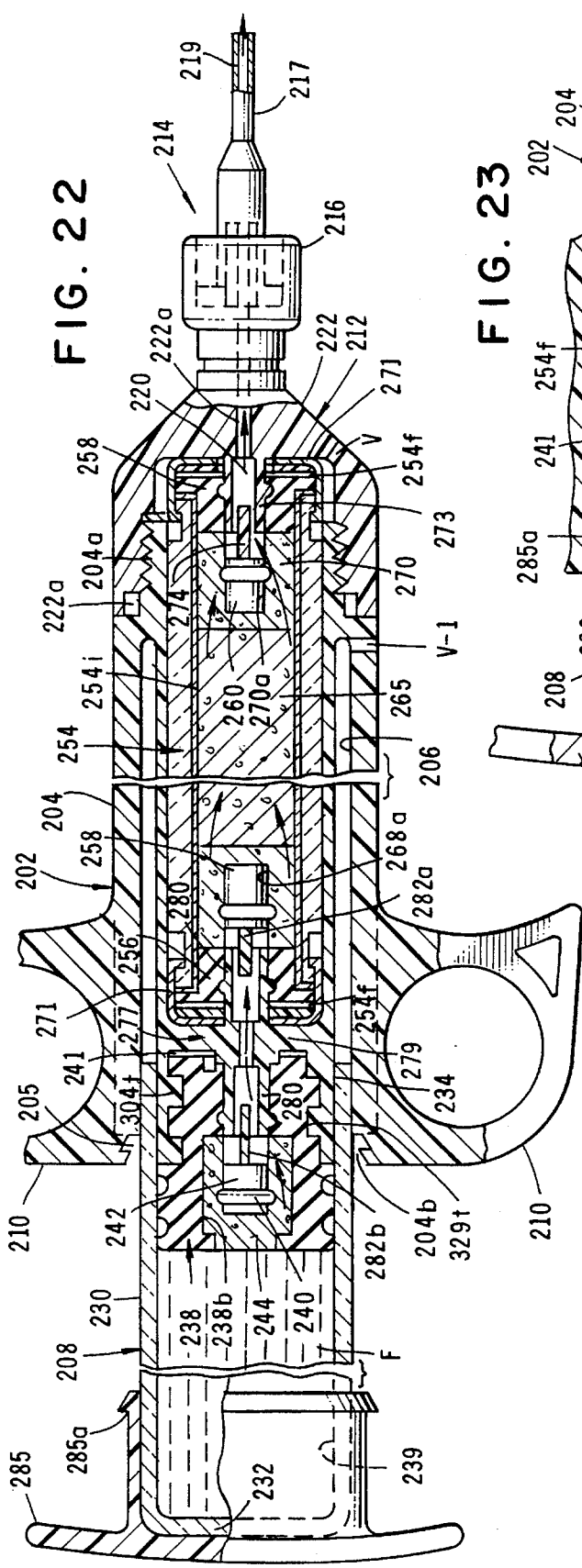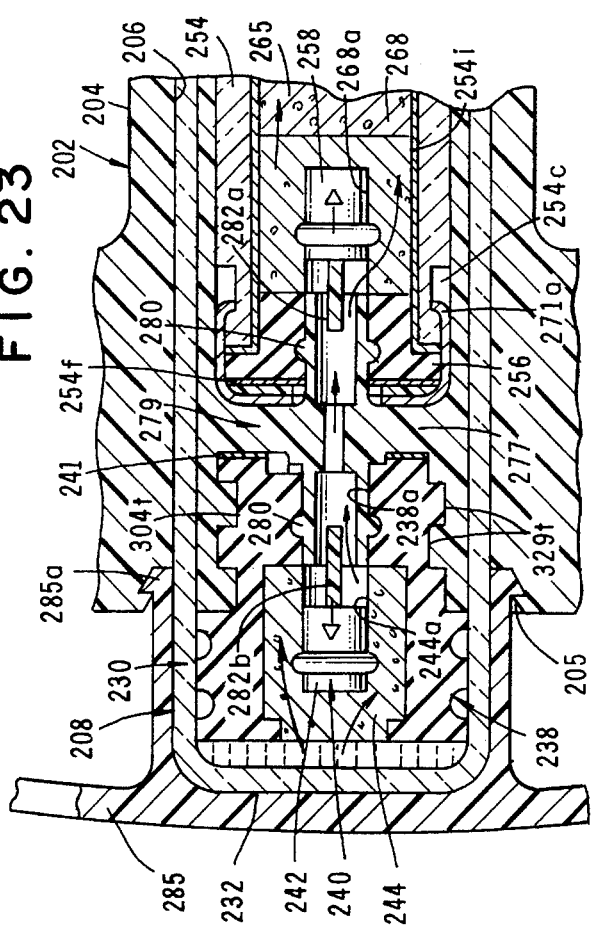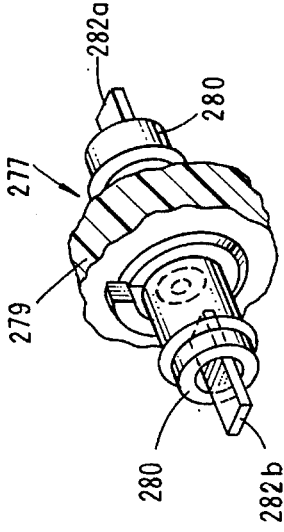

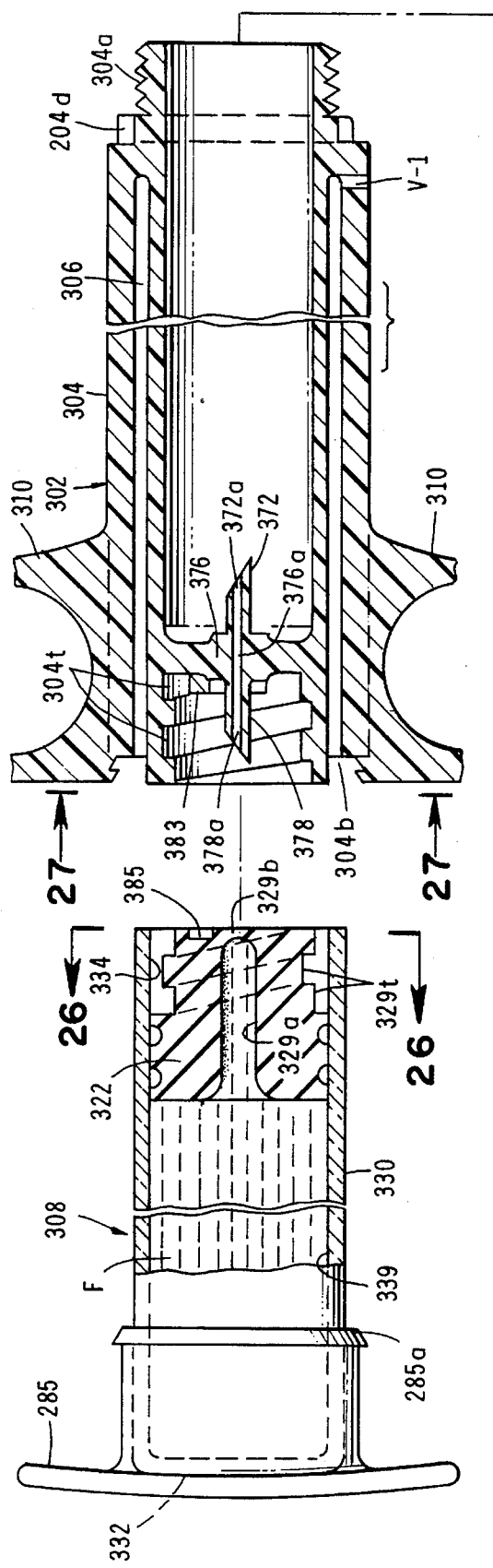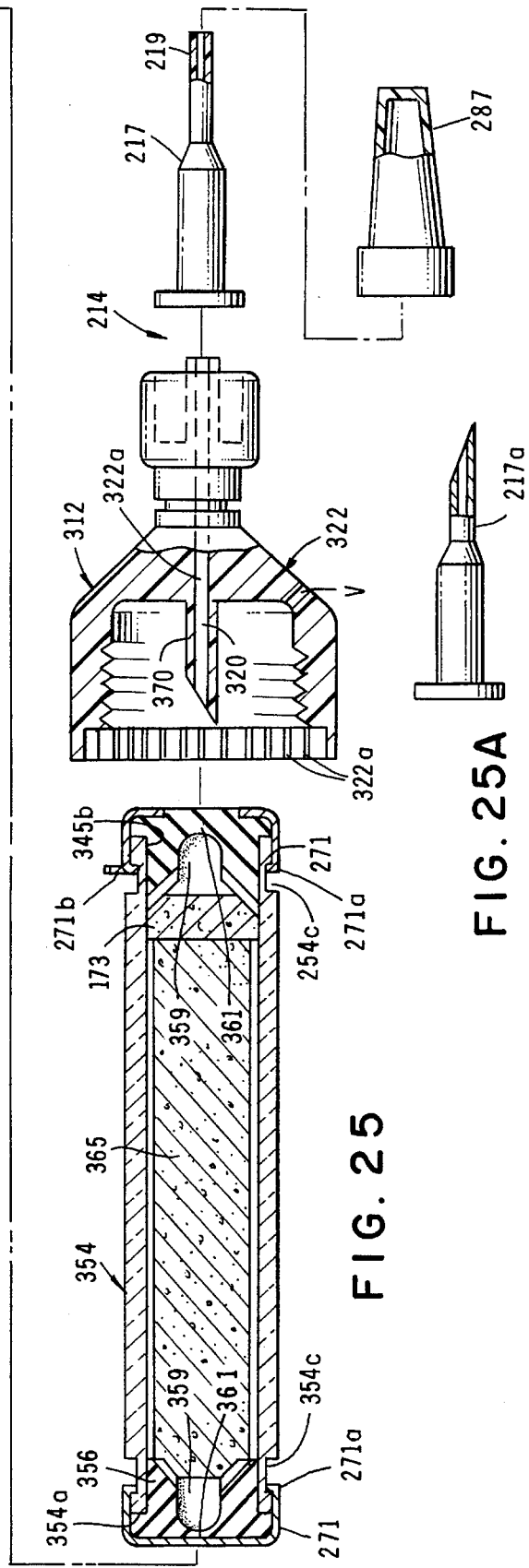

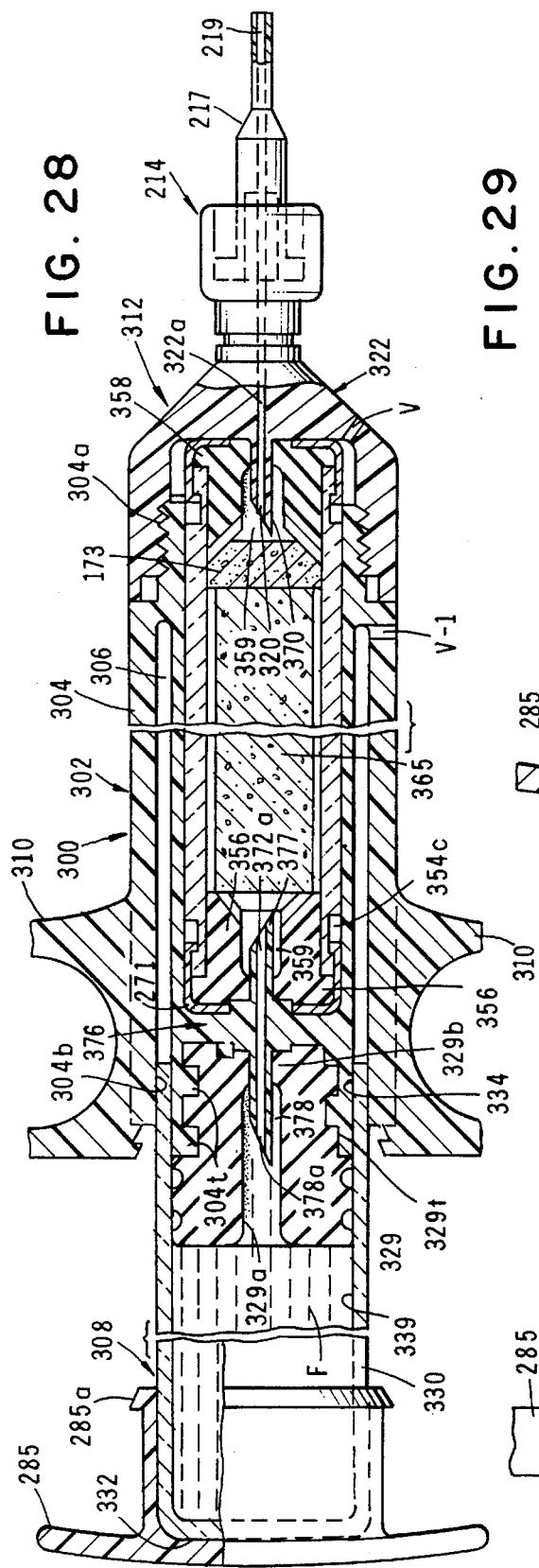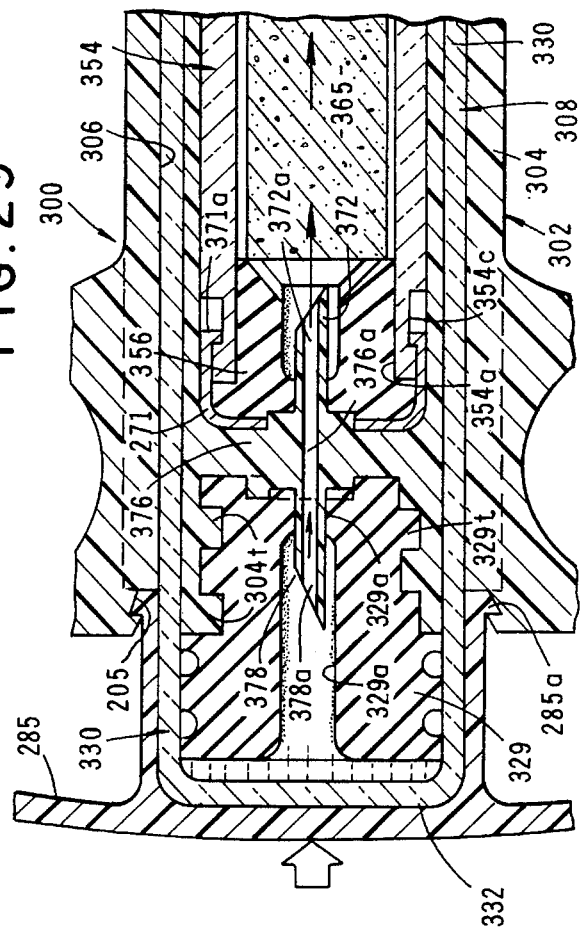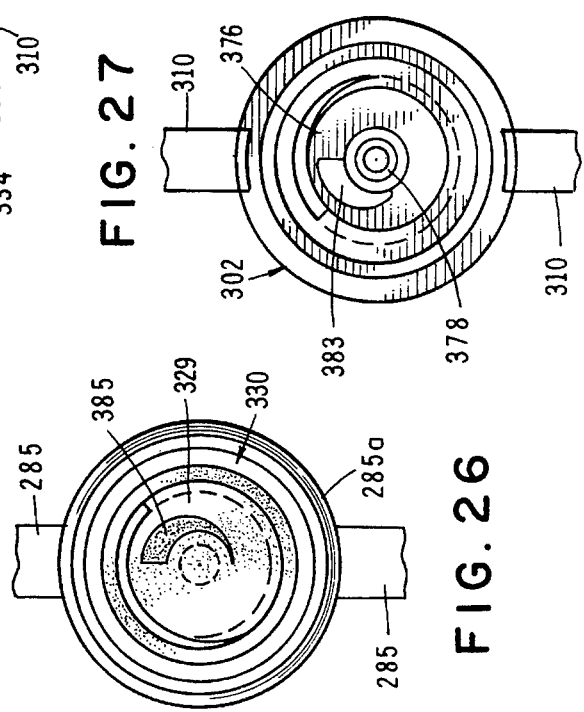

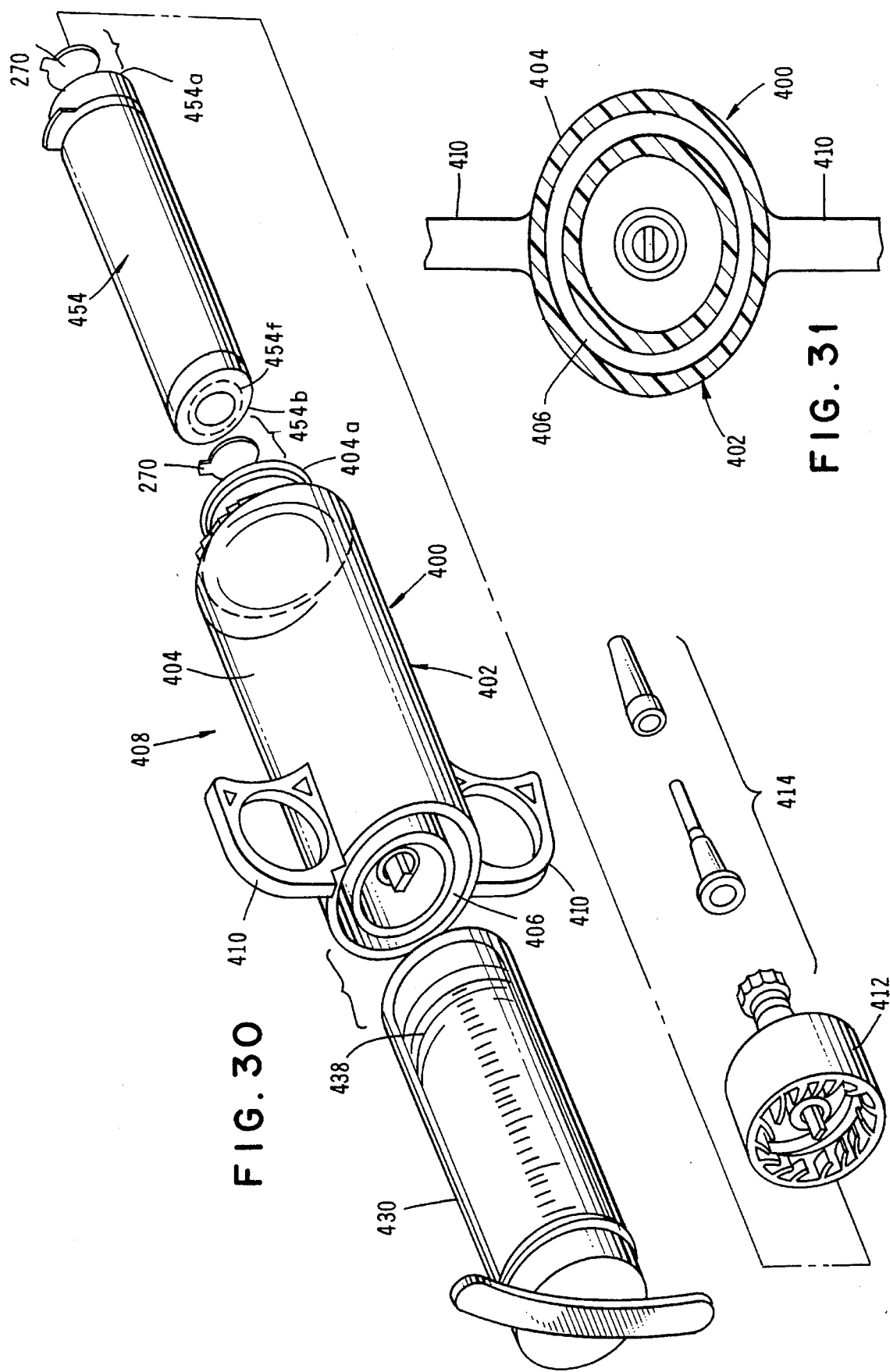

MIXING AND DELIVERY SYRINGE ASSEMBLY

This is a Continuation-In-Part of United States application Ser. No. 07/930,749 filed Aug. 13, 1992, now U.S. Pat. No. 5,330,426.

BACKGROUND OF THE INVENTION

1. Field of the Invention

The present invention relates generally to syringes of the character used to administer drugs by injecting them into subcutaneous tissue. More particularly, the invention concerns a syringe of novel design in which a first component, such as a sterilized diluent, can be intermixed with a second component, such as a drug to form a beneficial agent which can be dispensed directly from the syringe.

2. Discussion of the Invention

Hypodermic syringes are commonly used for injecting into a patient beneficial agents, such as drugs in liquid form. Typically, the beneficial agent to be injected is drawn into the syringe from another container, such as a glass vial, bottle or the like having a pierceable, self-sealing stopper. When the beneficial agent, such as a pharmaceutical, is in powder form prior to injection, it must be mixed with a carrier liquid or diluent, such as saline solution, dextrose solution and sterilized water.

Mixing of powdered pharmaceuticals with the carrier liquid has been accomplished in several ways, many of them being quite crude. For example, a common practice is to inject a small quantity of the liquid carrier into the vial to dissolve the powdered component. Then, using a cannula and syringe, the solution thus formed is injected into a larger container containing the liquid carrier. This method is quite tedious and provides substantial opportunities for contamination and error.

Because infusion of medicaments is most often accomplished in a hospital environment, it is the nurse, doctor or medical technician who mixes the drug and diluent, usually at a time shortly before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

In the past several attempts have been made to provide a syringe apparatus in which separate components can be intermixed prior to patient injection. Exemplary of such prior art devices are those disclosed in U.S. Pat. No. 2,724,383 issued to Lockhart; in U.S. Pat. No. 3,336,924 issued to Sarnoff, et al and U.S. Pat. No. 3,477,432 issued to Shaw. The Lockhart apparatus includes segregating compartments in the form of connecting, interfitting containers with associated cannula means which are manipulatable simultaneously so as to provide intercommunication between the compartments via the cannula means. The components to be mixed are stored in the interfitting containers and then are intermixed by suitably manipulating the containers. The device can be brought into "administering" condition by withdrawal of one of the empty containers to produce a hypodermic syringe type structure.

Sarnoff, et al. discloses several types of syringe packages, each comprising a vial containing a medicament, a stopper closing the vial, a connector member attached to the vial and extending beyond the stopper, and a syringe interconnected to the connector member. In one form of the Sarnoff invention, the needle of the syringes is partially embedded in the stopper. In another form of the invention, a double needle unit is carried within the connector member so that one needle can penetrate the stopper on the vial and the other can penetrate a stopper on a second container. In this last described embodiment, the double needle unit provides the flow path between the vial and the second container so that component mixing can occur.

In the Shaw patent various versions of combined mixing and injecting syringes are disclosed. The Shaw device enables intermixing of two ingredients which may be powders or liquids and provides for the injection of the mixture after the mixing step has been accomplished.

The apparatus of the present invention provides a totally new and novel approach to precisely intermixing two components and then expelling the mixture from the device through a needle or blunt cannula. More particularly, the apparatus comprises a housing within which an immobilized drug cartridge containing a selected drug or other beneficial agent can be inserted. One end of the housing is open and the opposite end is provided with an inwardly extending needle and an outwardly extending blunt end cannula. A diluent assembly including a sealed vial is then inserted into the open end of the housing and urged telescopically inward of the housing. This causes a double ended needle to simultaneously pierce the sealed vial and a rear seal provided on the drug cartridge thereby placing the vial and the drug cartridge in fluid communication. A continued inward force on the diluent assembly will cause the inwardly extending needle of the housing to pierce the forward seal of the drug cartridge, placing the interior of the drug cartridge in fluid communication with the blunt end cannula. As the diluent flows through the drug cartridge, it will controllably intermix with the immobilized drug forming an injectable solution which can be expelled from the device via the blunt ,end cannula.

SUMMARY OF THE INVENTION

It is an object of the present invention to provide a device for precisely intermixing a first component, such as a parenteral liquid, with a second component, such as a pharmaceutical, to form an injectable solution which can be dispensed from the device following mixing.

It is another object of the invention to provide a device of the aforementioned character in which the first and second components can be separately stored in sealed containers until they are coupled with the dispensing portion of the device for mixing and subsequent dispensing.

Another object of the invention is to provide a device as described in the preceding paragraphs in which the second component which can be any type of beneficial agent such as a drug, a pharmaceutical or a biological agent is removably affixed to a scaffold such as a rigid substrate which can be safely and conveniently stored within a sealed container until it is to be mixed with the second component.

It is an object of the present invention to provide an apparatus of the character described in the preceding paragraph which provides the opportunity to add in a sterile environment to a diluent or other parenteral fluid contained within a glass vial, selected elements, chemical compounds and biologically active materials, including drugs, medicaments, biological agents, and other therapeutic agents (additives). This addition is accomplished by removably affixing the selected additives to various forms of support structures or scaffolds which can be placed within a sealed container which can, in turn, be placed in fluid communication with the glass vial. In this way, the diluent within the glass vial can expeditiously be rendered therapeutically active upon reacting and releasing of the additive carried by the substrate into the diluent.

Another object of the invention is to provide an apparatus; of the character described in which the adding means, including the scaffold which carries the second component, or additive, is maintained within a completely sterile environment within the sealed container until immediately prior to the releasing and controlled mixing of the additive and the diluent.

Another object of the invention is to provide an apparatus of the class described in which a wide variety of selected additives can be removably affixed to the scaffold or substrate that is stored within the sealed container for controlled intermixing with the liquid contained within the glass vial.

Another object of the invention is to provide a device of the aforementioned type in which toxic or other hazardous compounds, including those with short therapeutic lives can be separately and safely stored until immediately prior to their use following being intermixed with the liquid compound contained within the diluent glass vial.

Another object of the invention is to provide a device of the character described in the preceding paragraphs in which toxic or other hazardous compounds which are to be intermixed with the liquid component can be separately and safely handled during the manufacture of the substrate portion of the device and in which the substrate carrying the hazardous materials can, following manufacture, be safely stored within the sealed container until time of use.

Another object of the invention is to provide a device of the class described in which the additive or beneficial agent components, such as a drug or pharmaceutical, can be uniformly deposited or otherwise removably affixed to the scaffold or additive support in a manner to maximize easy releasability and separation of the additive and complete intermixing thereof with the liquid component.

Another object of the invention is to provide a mixing and dispensing device which is of simple construction and is easy and safe to use by relatively unskilled technicians.

Another object of the invention is to provide a device of the aforementioned character in which precise mixing of the first and second components is automatically accomplished by the telescopic movement of a sealed vial containing the first diluent component into a hollow housing which supports the sealed container housing the scaffold upon which the second component is immobilized.

Another object of the invention is to provide a device as described which is provides with a swivel, leur-type fitting for interconnection therewith of a blunt cannula.

Another object of the invention is to provide a device as described in the preceding paragraphs in which the vial is positively coupled with the syringe body.

Another object of the invention is to provide a device as described in the preceding paragraph in which the mixed solution is automatically and controllably dispensed from the device as a result of the telescopic movement of the sealed container into the hollow syringe housing.

Still another object of the invention is to provide a device of the class described which embodies a minimum number of moving parts and one which can be inexpensively manufactured in quantity so that it can be economically disposed of after use.

BRIEF DESCRIPTION OF THE DRAWINGS

FIG. 1 is a generally perspective, exploded view of one form of the mixing and dispensing device of the present invention.

FIG. 2 is an enlarged, generally perspective, exploded view of a sealed container which contains the second component such as a drug or other beneficial agent which is to be intermixed with the first component such as a diluent which is contained in the first container shown in the upper portion of FIG. 1.

FIG. 3 is a generally perspective, exploded view illustrating the manner in which the first and second containers of the device are mated with the hollow housing portion of the device used to dispense the intermixed solution.

FIG. 4 is a generally perspective view of the dispensing housing portion of the device showing the second container containing the beneficial agent disposed within an internal chamber of the dispensing housing.

FIG. 5 is an enlarged, side-elevational view of one form of the device of the present .invention partly broken away to show internal construction.

FIG. 6 is a cross-sectional view taken along lines 6—6 of FIG. 5.

FIG. 7 is a side-elevational view partly in cross-section similar to FIG. 5 but showing the first and second component containers of the invention mated with the dispensing housing portion of the device.

FIG. 8 is cross-sectional view taken along lines 8—8 of FIG. 7.

FIG. 15 is an enlarged, cross-sectional view of the cartridge which is positioned within the syringe body depicted in phantom lines.

FIG. 16 is a cross-sectional view of the fluid container and drug cartridge mounted within the syringe body.

FIG. 17 is a generally perspective view of the sealing plug and valve operating means of the drug cartridge.

FIG. 18 is a generally perspective view of still another form of the device of the invention.

FIG. 19 is a generally perspective, exploded view of the device shown in FIG. 18.

FIG. 20 is a view taken along lines 20—20 of FIG. 19.

FIG. 21 is a cross-sectional view taken along lines 21—21 of FIG. 20.

FIG. 22 is an enlarged, cross-sectional view of the assembled device shown in FIG. 18.

FIG. 23 is an enlarged fragmentary, cross-sectional view of the left-hand portion of the device as viewed in FIG. 22 showing the fluid container fully inserted into the syringe housing.

FIG. 24 is a fragmentary perspective view of the valve operator assembly of the device as shown in FIG. 22.

FIG. 25 is a cross-sectional, exploded view of still another embodiment of the invention.

FIG. 25A is a side view, partially in cross-section, showing an alternate form of cannula for use with the apparatus shown in FIG. 25.

FIG. 26 is a view taken along lines 26—26 of FIG. 25.

FIG. 27 is a view taken along lines 27—27 of FIG. 25.

FIG. 28 is a cross-sectional view of the device shown in FIG. 25 in an assembled configuration.

FIG. 29 is an enlarged, cross-sectional view of the left-hand portion of the device shown in FIG. 28 with the fluid container fully inserted into the syringe housing.

FIG. 30 is a generally perspective, exploded view of yet another embodiment of the invention.

FIG. 31 is an enlarged, cross-sectional view of the housing and adding means of the form of the invention shown in FIG. 30.

Figure 32:
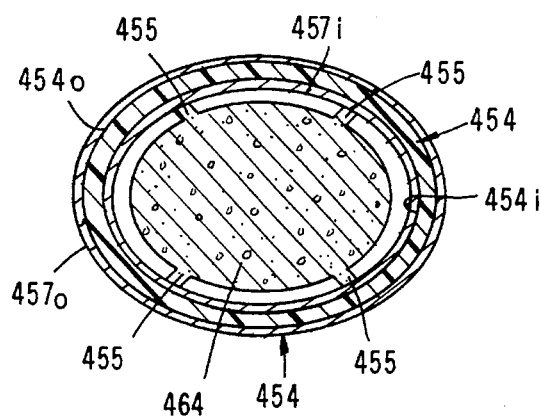

FIG. 32 is an enlarged, cross-sectional view of the adding means of the device shown in FIG. 30.

Figure 32A:
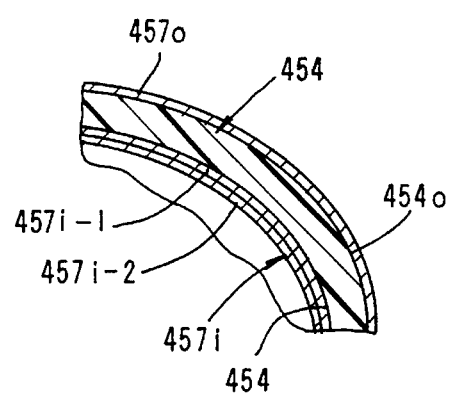

FIG. 32A is an enlarged, fragmentary view showing the inner and outer coatings applied to the inner and outer walls of the cylindrical member which comprises a part of the adding means.

Figure 33:
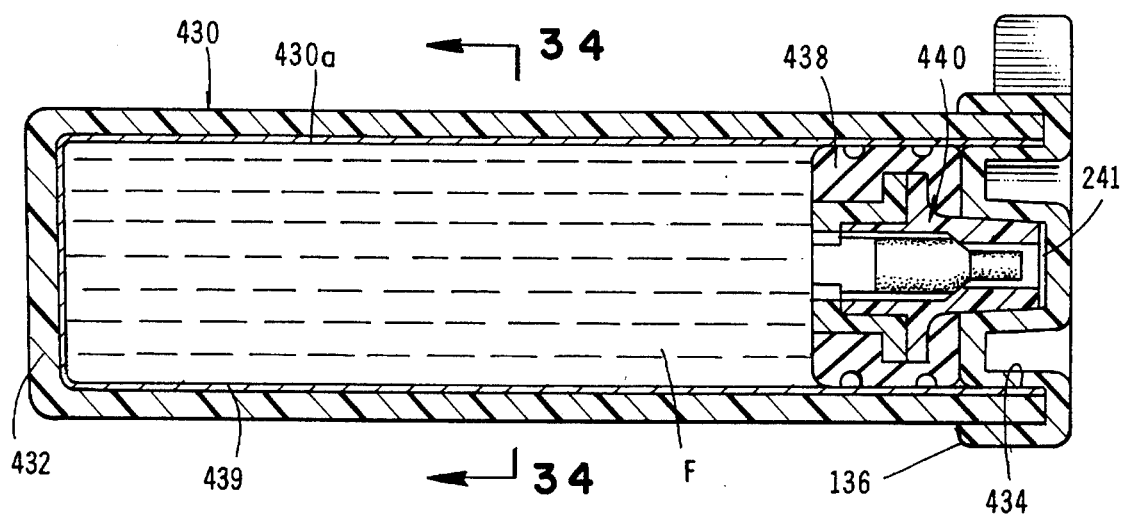

FIG. 33 is an enlarged, cross-sectional view of the fluid container portion of the device shown in FIG. 30.

Figure 34:
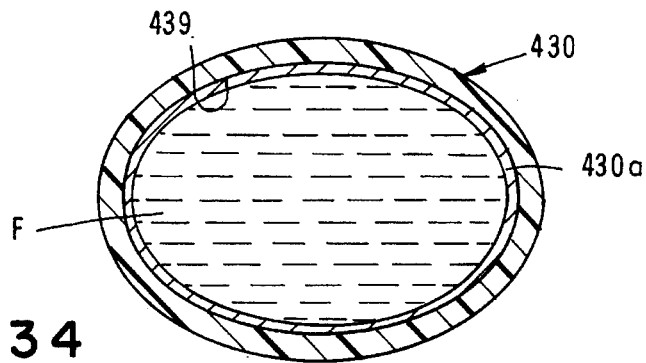

FIG. 34 is a cross-sectional view taken along lines 34—34 of FIG. 33.

DESCRIPTION OF THE INVENTION

In the paragraphs which follow, wherein the device of the invention will be discussed, the following terms will have the following meanings:

Element—any of the fundamental substances that consist of atoms of only one kind and that singly or in combination constitute all matter.

Additive—the element, compound, substance, agent, biologically active material, pharmaceutically active material or other material which is to be added to the fluid contained in the container means of the device of the invention.

Parenteral Fluid—any solution which may be delivered to a patient other than by way of the intestines, including water, saline solutions, alkalizing solutions, dextrose solutions, acidifying solutions, electrolyte solutions, reagents, solvents and like aqueous solutions.

Beneficial Agents—any drug, medicament, pharmaceutical, medical polymer, enzyme, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, co-factors, inhibitors, lectins, hormones, hormone producing cells, receptors, coagulation factors, anti-fungal agents, growth enhancers, histones, peptides, vitamins, drug, cell surface markers and toxins, among others known to those skilled in the art. Of the group of biologically active materials described, proteins are of utmost current interest because of the large molecule genetically engineered biopharmaceuticals as those species to be immobilized on the additive carriers hereinafter to be described. A discussion of the use of biomosic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a scaffold, a functional support, or carrier, an anchorage, a deposition site or element holder, with or without some type of intermediate matrix such as an azlactone functional material to provide a reactive intermediate support as described in U.S. Pat. No. 4,871,824, in EPO Application 0 392 735 A2 and in EPO Application WO 88/0706 2.

Additive Presentation Means—any means such as a scaffold, functional support or substrate for presenting the additive to the fluid flowing through the device. The scaffold or functional substrate can comprise a polymer, copolymer, and inter-polymer, a ceramic, a crystal sponge, a carbon based matrix, a celullosic, glass, plastic biomosaic polymers, azlactone-functional materials such as coatings, polymer beads, adduct beads, carboxylate-functional polymer beads, gums, gels, filaments and like carriers.

Figure 9:
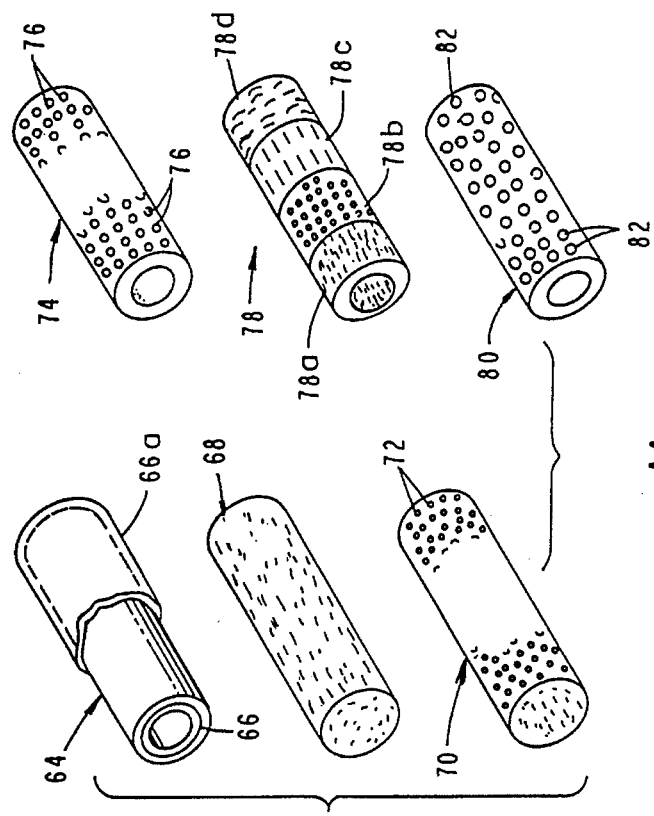
FIG. 9 is a generally perspective view of various forms of the supporting substrate or additive scaffold of the invention upon which the second component is removably affixed.
Figure 11:
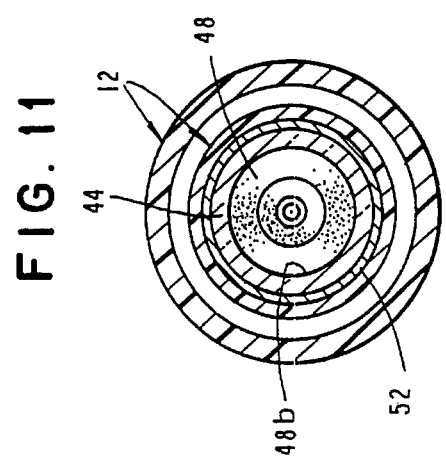
FIG. 11 is a cross-sectional view taken along lines 11—11 of FIG. 10.

The adding means of the invention can take several different forms such as those illustrated in FIG. 9. However, in its preferred form, the adding means comprises a microstructure with interconnecting voids such as a cylindrically shaped, microporous, polymeric functional support structure 50 (FIG. 2) to which various additives, including beneficial agents such as drugs, biologically active materials, and various chemical elements and compounds can be releasably connected. These additives are carried by the structure and extend into the voids in a manner such that, as the liquid within the second container, such as a diluent, reagent or other aqueous solvent flows around and about the support assembly, in the manner presently to be described, the additives will be presented to the liquid flow and efficiently added to the liquid.

The additives themselves can also take various physical forms including liquid, solid, granular, powder, particle, gel, wax hydrocolloid carriers, such a gum film, tablet, crystalline, emulsions, microcrystalline, microcapsules, microspherical, spray dried compounds and lypohilized compounds and saturants. The additives can be removably connected to, immobilized on, impregnated within or supported by support means in a number of ways. The additives can be chemically or mechanically attached, affixed, or bound directly or indirectly through cooperation with an intermediate matrix. They can be captured, affixed, linked, or cross-linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited suspended or occluded within voids, cells, tubules and interstices formed in the support. One important method for removably affixing the additive to the functional support means includes treating the functional support means with a compound having reactive functional groups such as azlactone functional compounds with their high binding capacity. In certain applications, the biologically active material can be bound at the surfaces of biomosaic polymers in the manner described in EPO Patent No. 0 430 517 A2. Similarly, graft copolymers can be used in the manner described in U.S. Pat. No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking bioseparation, diffusion, washing, disintegration, erosion, disassociation, desorbsion, solubilization, leeching, enzymatic cleavage, biological reaction, osmosis, separated from ring opening materials and like separation means.

An important function of the functional support, or matrix is to provide the desired interaction between the additive and the elusion fluid. The matrix can be appropriately tailored to provide the ability for affinity attachment of the target component or molecule for subsequent coupling with the desired beneficial agent to be selectively absorbed and then to be desorbed from the matrix at time of use. Because some very specific interactions with the target molecule are desired, the choice of the matrix material is extremely important for isolation and selectivity or specificity of the affinity activity. Further, the proper choice of materials for the matrix, including the incorporation of an azlactone functional group into the matrix can be useful for coupling affinity ligands without the need for prior activation. Target components, such as proteinacious ligands, can be readily coupled to the matrix under a variety of buffer, salt and concentration conditions, with efficient coupling generally being achieved at a pH of 7 or greater.

The incorporation of spacer molecules between the matrix and the ligand can also improve the interaction of an affinity ligand with its target molecule. Additionally, the optimum conditions for coupling small molecules may be quite different from those of large molecules such as proteins. Accordingly, the influences of concentration, pH, coupling solvent and possible condensation agents may be required for efficient coupling of small ligands.

Of special interest, the azlactone ring, which can be an integral part of the polymer matrix, reacts with a nucleophile in a ring-opening reaction and couples the nucleophile to the support scaffold via a strong stable amide bond. This covalent bond results in low ligand leaching. The matrix support is preferably very hydrophilic to minimize non-specific binding and should contain high surface area and pore volume for facilitating macro-molecular access and rapid diffusion. For subsequent elution efficiency the matrix should be desired for medium of low pressure flow conditions.

The coupling buffer, storage preservation solution and elution solvents and their respective composition and concentration can be selected and tailored so that it is the most conducive for the ligand and/or for its coupling and decoupling to and from the matrix scaffold support.

DESCRIPTION OF THE INVENTION

Referring to the drawings and particularly to FIGS. 1, 2, 3 and 4, the device of the present invention for intermixing a first fluid component with a second component and then for dispensing the mixture therefrom is shown in an exploded form in FIG. 3. The device of the embodiment of the invention there shown comprises a hollow housing 12 having a longitudinally extending opening 14 in the wall thereof and first and second ends 16 and 18. Opening 14 is initially closed by a pealably removable, sterile barrier patch 12b. As best seen by referring to FIG. 3, the second end 18 of housing 12 is temporarily closed by a removable cap 12c, while the first end 16 is closed by a closure wall 20. Connected to closure wall 20 and extending outwardly from housing 12 is a blunt end cannula 22 which forms the fluid outlet of the housing 12. Cannula 22 has an internal flow passageway 24 which is in communication with a fluid flow passageway 26 provided in an inwardly extending cannula 28 which is also connected to end closure wall 20. Passageway 24 is temporarily closed by a cannula cap 22a.

Container means which can be removably interconnected with housing 12 is provided to contain a first fluid component such as a diluent or other parenternal fluid 27 (FIG. 5). This container means is most clearly illustrated in FIG. 1 and comprises a glass vial 30 having a closed end 32 and an open end 34. Open end 34 of vial 30 can be closed by a penetrable plug 36 which can be constructed of any suitable needle puncturable elastomeric material such as soft rubber. In a manner presently to be described, plug 36 is telescopically movable within an internal chamber 38 of glass vial 30. For purposes of sterile presentation, a tear-away cap 40 is provided to overlay both plug 36 and open end 34 of vial 30. Disposed intermediate cap 40 and plug 36 is flow means for permitting the fluid contained within the glass vial to flow outwardly thereof after cap 40 has been removed from the vial assembly. Flow means is here provided in the form of a generally frustro-conically shaped, collapsible wall element 42. As best seen by referring to FIG. 5, element 42 includes a circular base flange portion 42a which is adapted to engage the outer surface of plug 36 and a circular end wall 42b through which a double ended cannula or needle 47 extends. Needle 47 includes a fluid passageway 47a which, in a manner presently to be described, permits fluid contained within glass vial 30 to flow outwardly of the vial interior toward housing 12 following mating of the first container means with the dispensing housing 12.

Forming an extremely important aspect of the device of the present invention is adding means for adding a second component such as a drug or other beneficial agent to the first fluid component contained within vial 30. In the form of the invention shown in the drawings, the adding means comprises an assembly of the character best illustrated in FIG. 2. More particularly, the adding means here comprises a cartridge 44 having first and second open ends 44a and 44b. Open end 44a is sealed by a first sealing means while open end 44b is sealed by a second sealing means. The first and second sealing means are here shown as penetrable seals 46 and 48 respectively which are sealably received within the open ends of cartridge 44. Seals 46 and 48 can be constructed of any suitable non-coring needle puncturable elastomeric material such as a soft rubber or silicone.

Disposed internally of cartridge 44 is the additive carrying means of the invention here shown as a cylindrically shaped porous substrate or scaffold 50. Substrate 50 is preferably a microporous, polymeric functional support to which various additives including beneficial agents such as drugs, biologically active materials, and chemical elements and compounds can be releasably connected. These additives are supported by the scaffold or substrate 50 in a manner such that as the liquid component contained within the glass vial, such as a diluent, reagent, or aqueous solvent flows around, about and through the scaffold, the additives will be reacted, released, separated and intermixed with the liquid component. In a manner presently to be described, the additives are uniquely presented to the fluid flow so that they can be efficiently added to the first liquid component contained within the glass vial. Surrounding cartridge 44, which may also be constructed of glass, plastic or other suitable material is a shrink-wrap label or polyolefin overwrap 52 having indicia imprinted thereon identifying the additive or beneficial agent that is immobilized on the scaffold 50. Overwrap 52 also functions to retain pierceable plugs 46 and 48 in place within vial 44.

Figure 10:
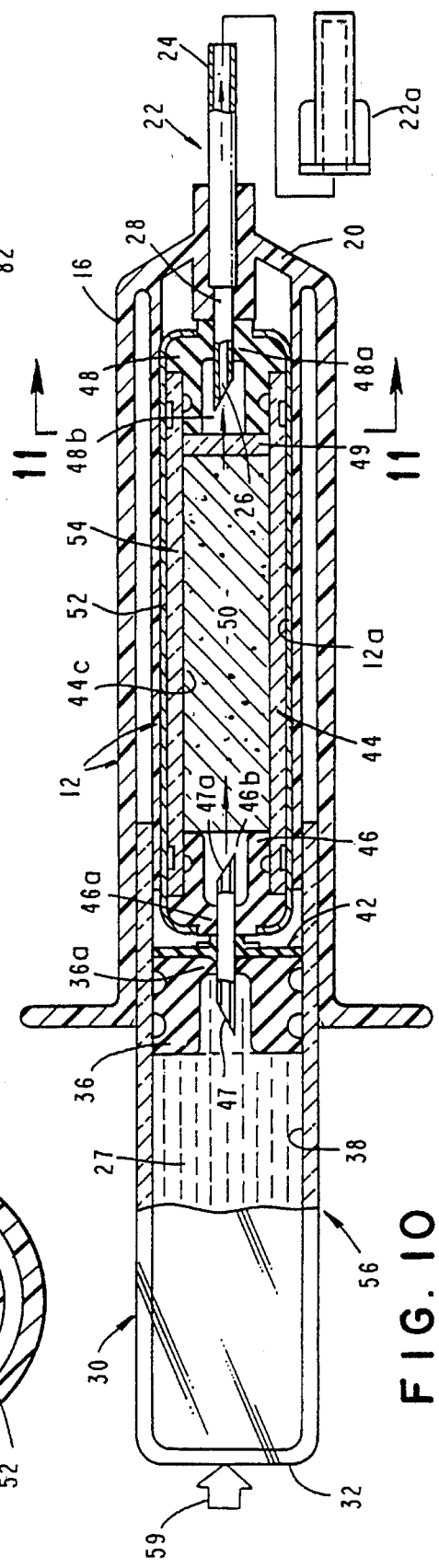
FIG. 10 is an enlarged side-elevational view partly in cross-section similar to FIG. 7 but showing the position of the component parts after the first container has been telescopically moved inwardly of the dispensing housing.

Turning now to FIGS. 3, 5, and 7, the adding means, which is generally identified in FIG. 3 by the numeral 54, is receivable within the interior chamber 12a of the dispensing housing 12 through the opening 14 provided in the wall thereof. As indicated in FIG. 3, following removal of the sterile barrier patch 12b which sealably covers opening 14, the assemblage 54 can be installed through the opening 14 so that it securely nests within internal chamber 12a in the manner shown in FIG. 7. Assemblage 54 can be of a polarized configuration well known in the art, such as by an indexed spacer, so that the assemblage can be received with chamber 12a in only one orientation. The first container means which is generally identified in FIG. 5 by the numeral 56 is adapted to be mated with housing 12 in a manner now to be described. The first step in the mating process comprising the step of removing barrier cap 40 so as to form the subassemblage identified in FIGS. 3 and 7 by the numeral 58. After barrier cap 12c is removed, the plugged end of assemblage 58 is then telescopically inserted into the open end 18 of housing 12 in the manner shown in FIG. 7 so as to maintain a sterile fluid path. Inward pressure directed against subassembly 58 in the direction of the arrow 59 in FIG. 10 will cause several events to occur simultaneously. One such event, as illustrated in FIG. 10, comprises the collapsing of wall 42 of the flow means in a manner such that double ended needle 47 will simultaneously pierce portion 36a of penetrable plug 36 of the container means and piercable portion 46a of sealable plug 46 of the adding means. This places the interior of glass vial 30 in fluid communication with the internal chamber of cartridge 44 so that fluid contained within the glass vial can flow inwardly into the inner chamber 44c of cartridge 44 and then around, about and through substrate 50. The exertion of a continued inward pressure against the glass vial in the direction of arrow 59 will cause needle 28 of housing assembly 12 to penetrate portion 48a of plug 48 of the adding means thereby permitting fluid flow between the adding means and the outlet or cannula 22 of the dispensing subassembly or syringe housing 12. This combination of needle 28 and cannula 22 comprises a second flow means of the invention for permitting fluid flow between the adding means and the outlet of dispensing housing 12.

As an inward pressure on the glass vial is maintained, penetrable plug 36 will travel longitudinally relative to the glass vial inwardly thereof. This will cause the liquid contained within the glass vial to flow rapidly through the passageway 47a in double-ended needle 47 and into the internal chamber 44c of cartridge 44. Fluid flowing through piercable plug 46 will be distributed in a uniform outwardly direction via portion 46b of the plug and the proximal interface of porous support 50. As the fluid passes through the internal chamber of the cartridge, it will flow around, about and through substrate 50 in a manner to cause the additive immobilized thereon or otherwise removably affixed thereto to separate and thoroughly intermix with the liquid to form an injectable solution. The pressure of the fluid flowing through the adding means will also cause controllable ejection of the injectable solution through passageway 24 of cannula 22. Portion 48b of plug 48 functions as a fluid collection means from a filter 49 and the distal interface well of substrate 50 to focus fluid flow toward passageway 26 of cannula 28. Filter 49, which may be a polyethylene, hydrophilic depth filter with a screen base, is interposed between scaffold 50 and plug 48. Filter 49 sealably engages the inner wall of glass ampule 44 and functions to trap particulate or gaseous matter which may be contained in the mixed solution. This particulate filter and gas containment means can be configured as desired for the particular application at hand.

Turning now to FIG. 9 various other forms of adding means or additive assemblies are there illustrated. For example, numeral 64 identifies an assembly comprising a plurality of layers 66 each of which is coated with the selected additive. In some instances a microporous membrane film or skin 66a envelops the assembly to permit contaminate free handling. The layers 66 are overlayed in the manner shown in the drawing to provide a multiplicity of exposed surfaces and alternatively spaced reaction sites which are exposed to the diluent as it flows through chamber 44c.

Numeral 68 designates a porous substrate with open interstitial cells or pores and interconnecting voids, such as a porous ceramic with various coatings containing one or more additives deposited within the voids. The selected additives such as elements, chemical compounds or drugs are contained within the deposited material and are deposited, or immobilized thereon with or without the use of an intermediate matrix by techniques well known to those skilled in the art. The additives contained within the voids are, of course, presented or exposed to the diluent, are separated from the scaffold and then are introduced into the sterile diluent or other liquid as it flows through chamber 44c.

Another form of additive assembly designated in FIG. 9 by the numeral 70 comprises a generally tubular member having a multiplicity of alternate sized pores 72 which are plugged with selected additives such as chemical compounds and beneficial agents, or medicaments.

Still another form of the additive assembly is identified in FIG. 9 by the numeral 74. This assembly comprises a cylindrical, porous plug-like member made up of a multiplicity of fused together microspheres 76 each of which is coated with a separation or reactive coating acting as useful reactive or adduct supports for the affinity attachment and subsequent release of an additive such as a biologically active material or other beneficial agents.

Another slightly more complex additive assembly is identified by the numeral 78. This assembly is made up of a plurality of spaced-apart, porous disk shaped wafers 78a, 78b, 78c and 78d each wafer being of the same or different construction and porosity and each having a multiplicity of reactive sites presenting to the liquid flow specially selected individual species of additives such as beneficial agents, elements or compounds so that multiple reactivities and selectivities and mixing can be achieved. With this construction, a wide variety of liquid flow rates, and complex sequential separations and priority staged substance introduction into the outlet cannula can be achieved by specially designing each of the wafers having unique affinity and separation characteristics that cooperate to make up the functional structural support.

The numeral 80 of FIG. 9 identifies yet another form of the additive means of the invention. In this form of the invention, a generally cylindrically shaped insoluble functional support means is formed from a biomosaic polymer 82 which may be porous or non-porous presenting a multiplicity of reactive sites for bioseparation of materials bound at the surfaces of the polymer.

Assemblies 64 through 80 which may be soluble or insoluble are intended to merely exemplify, not to limit, the wide variety of materials, constructions and techniques for drug compound or agent affinity and separation that can be used to introduce the desired additives into the liquid flow introduced into the internal chamber 44c of the adding means. Similarly vials 30 and 44 can be constructed of various materials other than glass such as plastic. In like manner housing 12 can be constructed from various materials including polyethylene, polyesters, polyamides, polycarbonates and the like.

After the diluent or other parenteral fluid is introduced into chamber 44c and mixed with the additive, the solution is dispensed from the device via cannula 22 to the environment of use.

Turning now to FIGS. 12 through 17, an alternate form of the device of the invention is there shown and generally designated by the numeral 100. The device of this latest embodiment of the invention is similar in many respects to the earlier described embodiments and comprises a hollow housing 112 having a longitudinally extending opening 114 in the wall thereof and first and second ends 116 and 118 (FIG. 16).

As best seen by referring to FIGS. 16 and 17, the second end 118 of housing 112 is open, while the first end 116 is closed by a closure wall 120. Connected to closure wall 120 and extending outwardly from the housing is a blunt end cannula 122 which forms a fluid outlet of the housing. Cannula 122 has an internal flow passageway 124 which is in communication with a fluid flow passageway 127 provided in an inwardly extending cannula 128 which is also connected to end closure wall 120.

Figure 12:
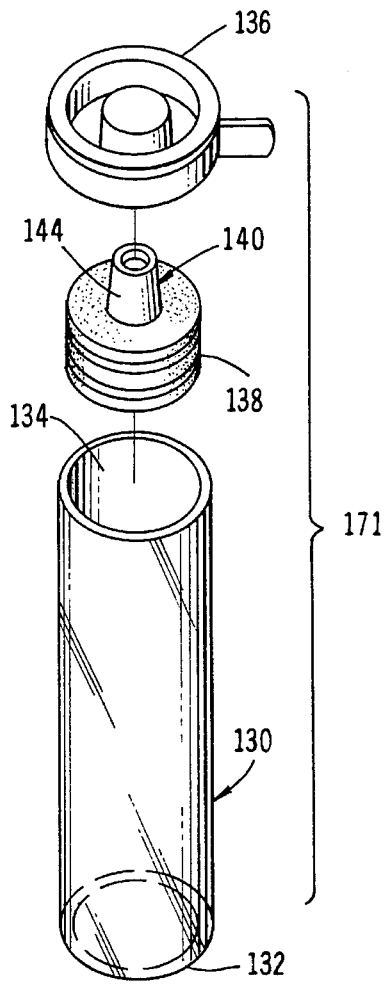
FIG. 12 is a generally perspective, exploded view of another form of fluid container of the invention.
Figure 13:
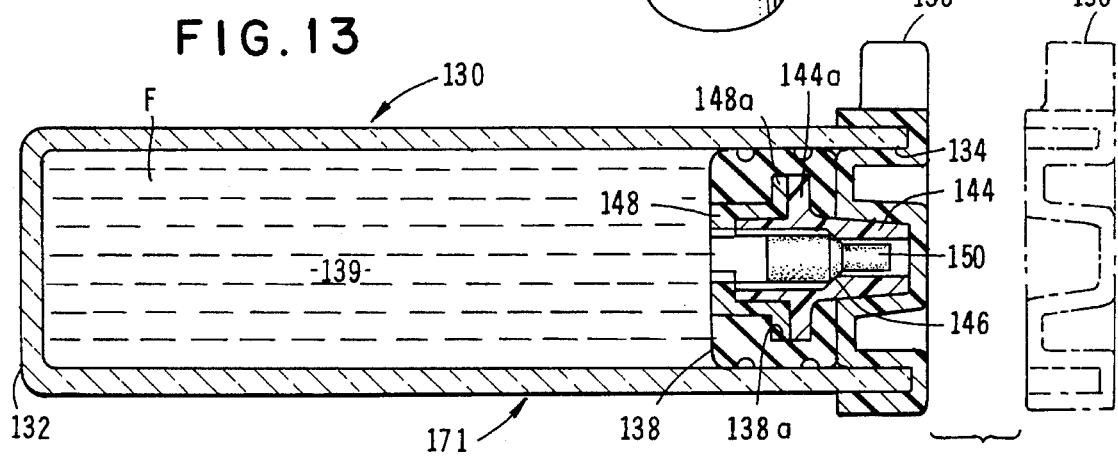
FIG. 13 is an enlarged, cross-sectional view of the fluid container shown in FIG. 12.

The container means of this latest form of the invention is of a slightly different construction which will be described presently. As illustrated in FIGS. 12 and 13, the container means comprises a container 130 which is adapted to contain a first fluid component such as a diluent or other parenteral fluid "F". Container 130 has a closed end 132 and an open end 134 within which the valve means is sealably mounted. Open end 134 of the container, or vial, 130 is normally closed by a sterile tear off type cap 136.

The valve means of the invention includes a plug 138 which is constructed of an elastomeric material such as soft rubber. In a manner presently to be described, plug 138 is telescopically movable within an internal chamber 139 of vial 130 between first and second positions. Disposed internally of plug 138 is a valve assembly 140 for permitting the fluid "F" contained within the vial to flow outwardly thereof after cap 136 has been removed from the vial assembly.

Valve assembly 140 here comprises a generally tubular shaped valve housing 144 having a valve seat 146 (FIG. 13). Valve housing 144 includes a circular shaped flange portion 144a which is receivable within a groove 138a provided in plug 138. A retainer member 148, which includes a flange 148a that is receivable within groove 138a, functions to retain housing 144 in position within plug 138. Telescopically movable within valve housing 144 is a valve member 150 which, in its open position, permits fluid contained within vial 130 to flow outwardly of the vial interior toward housing 112 following mating of the first container means with the dispensing housing 112.

Forming an extremely important aspect of the device of the present invention is adding means for adding a second component, such as a drug or other beneficial agent, to the first fluid component contained within vial 130. In the form of the invention shown in the drawings, the adding means comprises an assembly 153 of the character best illustrated in FIGS. 14 and 15. More particularly, the adding means here comprises a tubular member 154 having first and second open ends 154a and 154b. Open end 154a is sealed by a first sealing means while open end 154b is sealed by a second sealing means. The first sealing means comprises a hollow elastomeric plug 156 which is sealably received within end 154a of tubular member 154. Mounted internally of plug 156 is a valve operating means shown here as a support 160 and an operating stem 162 carried by support 160. The manner of operation of the valve operating means will be described in the paragraphs which follow. Second end 154b of the member 154 is closed by a plug 163 which is constructed of elastomeric material such as a soft rubber or silicone. Plug 163 is slitted at 163a to sealably receive cannula 128.

Disposed internally of tubular member 154 is the additive carrying means of the invention, here shown as a cylindrically shaped porous substrate or scaffold 165. Substrate 165 is preferably a polymeric microporous support of the character previously described to which various additives, including beneficial agents such as drugs, biologically active materials, and chemical elements and compounds can be releasably connected. In the instant form of the invention, the support medium is composed of a highly hydrophilic, porous and resilient cross-linked polymeric hydrogel. Based on the elastic nature of this material, the support medium can be classified as a semi-rigid gel. Certain forms of acrylic polymers exhibit resistance to compression under flow while maintaining high porosity and hydrophilicity.

In the present embodiment of the invention, the additives are supported by the scaffold or substrate 165 in a manner such that as the liquid component contained within vial 154, such as a diluent, reagent, or aqueous solvent, flows around, about and through the scaffold, the additives will be reacted, released, separated and intermixed with the liquid component.

Surrounding tubular member 154, which may be constructed of glass, plastic or other suitable material, is a shrink-wrap label or polyolefin overwrap 167 having indicia imprinted thereon identifying the additive or beneficial agent that is immobilized on the scaffold 165. Overwrap 167 also functions to retain plugs 156 and 163 in place within vial 154. As shown in FIG. 16, the adding means, or assembly 153, is receivable within the interior chamber of the dispensing housing 112 through the opening 114 provided in the wall thereof.

Figure 14:
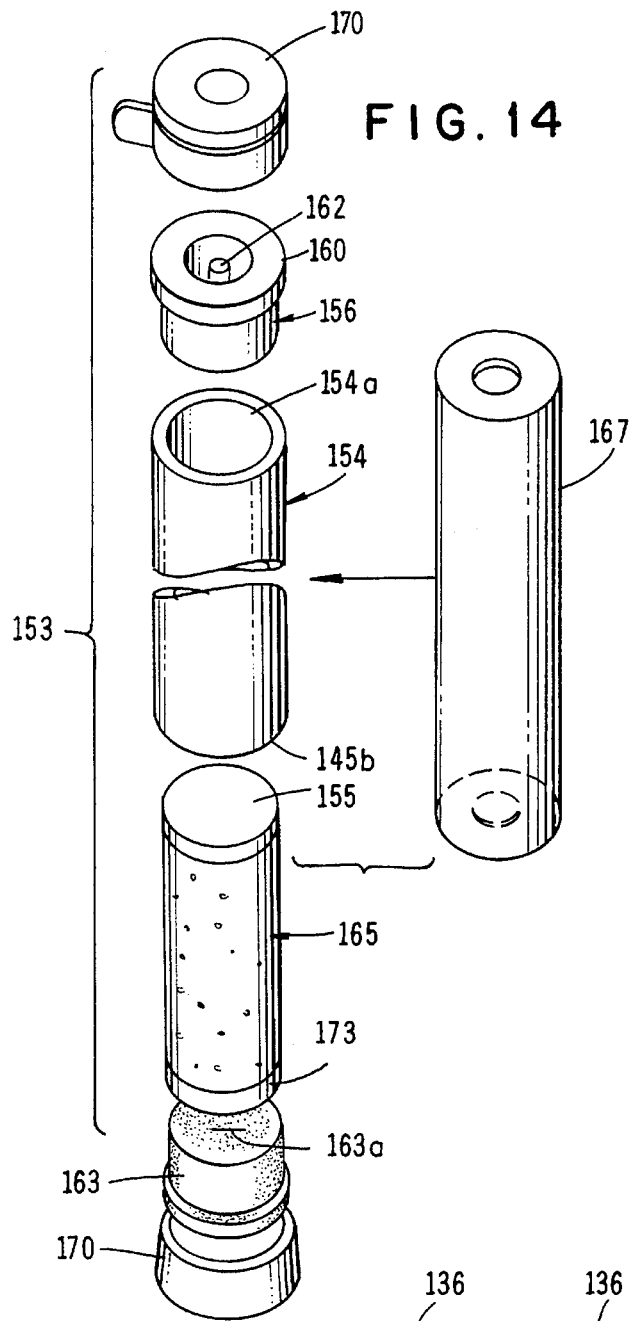
FIG. 14 is a generally perspective, exploded view of another form of adding means or drug cartridge of the invention.

Following the removal of the sterile tear-off caps 170 from each end of the assembly 153, which is illustrated in FIG. 14, the assembly is inserted into housing 112 in the manner shown in FIG. 15. Next the container means, which comprises assembly 171 (FIG. 12), is mated with housing 112 in a manner now to be described. The first step in the mating process is to remove barrier cap 136 from container 130. This done, the plugged end of the container subassembly is telescopically inserted into the open end 118 of housing 112 in the manner shown in FIG. 16 so as to maintain a sterile fluid path. Inward pressure directed against end wall 132 of the container assembly 171 will cause valve actuating member 162 to engage valve member 150 and move it into the valve open position shown in FIG. 16. This places the interior of container 130 in fluid communication with the internal chamber of tubular member 154 so that fluid contained within the container can flow inwardly into the inner chamber of the tubular member and then around, about and through scaffold 165. The exertion of a continued inward pressure against wall 132 of vial 130 will cause cannula 128 of housing assembly 112 to penetrate slitted plug 163 of the adding means thereby permitting fluid flow between the adding means and the outlet or cannula 122 of the syringe housing 112. This combination of cannula 128 and cannula 122 comprises a second flow means of the invention for permitting fluid flow between the adding means and the outlet of dispensing housing 112. As indicated in FIGS. 15 and 16, plug 163 is provided with the central, generally conically shaped, cored-out, or slitted portion 163a to expedite the insertion of cannula 128 into plug 163.

As an inward pressure on vial 130 is maintained, plug 138 will travel longitudinally of the vial. This movement of plug 138 will cause the liquid contained within the vial to flow rapidly through the valve means and into the internal chamber of tubular member 154 via porous distribution frit 155. Frit 155 comprises the flow control means of this embodiment of the invention for elution distribution and rate control of the fluid flowing into the internal chamber of the tubular member. Frit 155 can be constructed from any suitable material including porous polymers, porous glass and porous ceramics. As the fluid passes through the internal chamber of the cartridge, it will flow around, about and through substrate 165 in a manner to cause the additive immobilized thereon, or otherwise removably affixed thereto, to separate and thoroughly intermix with the liquid to form an injectable solution. The pressure of the fluid flowing through the adding means will also cause controllable flow of the injectable solution through passageway 124 of cannula 122 via filter means shown here as a filter 173 which is disposed within tubular member 154 proximate plug 163. The filter means here functions both as filter and a rate control member which in cooperation with frit 155 controls the residence time of the fluid within the internal chamber of member 154. Filter 173 may be a polyethylene, hydrophilic type filter designed to trap particulate or gaseous matter which may be contained in the mixed solution and promote secondary mixing. As before, this particulate filter and gas containment means can be configured as desired for the particular application at hand.

Turning now to FIGS. 18 through 24, still another form of the mixing and delivery syringe assembly of the present invention is there illustrated and generally identified by the numeral 200. This last form of the invention is similar in many respects to the embodiments previously described, but includes valving means of a different construction for controlling fluid flow into and out of the mixing chamber of the device. As best seen in FIGS. 18, 19, and 20, the apparatus of this last embodiment comprises a hollow housing 202 having an outer wall 204 provided with a longitudinally extending, circumferential channel 206 (FIG. 20). In a manner presently to be described, channel 206 closely receives the outer wall of the fluid container subassembly 208 of the apparatus as the fluid container is mated with the syringe housing. Connected to wall 204 and extending outwardly therefrom are oppositely disposed gripping elements 210, which are configured to receive the fingers of the user. The forward, or first end, 204a of wall 204 is threaded to threadably receive a closure cap assembly 212 within which is mounted a first valve operating means, the purpose and character of which will be described in the paragraphs which follow.

Integrally formed with cap assembly 212 and extending outwardly therefrom is a cannula assembly 214 which includes a cannula connector assembly 216 and a blunt end cannula 217. Cannula 217 has an internal flow passageway 219 (FIG. 20) which is in communication with a fluid flow passageway 220 provided in the previously identified valve operating means. As best seen in FIGS. 20 and 22, cap portion 222 of cap assembly 212 is provided with a fluid passageway 222a which interconnects passageways 219 and 220.

The container means of this latest form of the invention is of a slightly different valved construction and comprises a container 230 which forms a part of container subassembly 208. Container 230 is adapted to contain a first fluid component such as a diluent or other parenteral fluid "F" and has a closed end 232 and an open end 234 within which a valve means of slightly different construction is sealably mounted. Open end 234 of the container or vial 230 is normally closed by a sterile tear off type cap similar to the previously described cap 136. The valve means of the invention includes a plug 238 which is constructed of an elastomeric material such as soft rubber. As before, plug 238 is telescopically movable within an internal chamber 239 of vial 230 between first and second positions. Disposed internally of plug 238 is a valve assembly 240 for permitting the fluid "F" contained within the vial to flow outwardly thereof after the sterile closure cap has been removed from the vial assembly and frangible means, or frangible disk 241 has been ruptured (FIG. 22). Valve assembly 240 here comprises a valve member 242 which is sealably received within a central passageway 238a of plug 238. Plug 238 also includes an enlarged diameter central passageway 238b within which a porous member 244 is disposed. Member 244 is, in turn, provided with an internal chamber 244a which is configured to closely receive valve member 242 when the valve is in the open position shown in FIG. 22. When the valve is in the open position, fluid contained within vial 230 is permitted to flow through porous member 244 and outwardly of the vial interior toward housing 202 following mating of the first container means with the dispensing housing 202.

As was the case with the earlier described embodiments, adding means is provided for adding a second component such as a drug or other beneficial agent to the first fluid component contained within vial 230. In the form of the invention shown in FIGS. 18 through 24, the adding means comprises an assembly made up of a tubular member 254 having first and second open ends 254a and 254b and an internal coating 254i. Coating 254i may be of a single layer or multiple layers and, depending upon the materials, used can comprise a barrier to vapor transmission and oxygen permeation. In a manner later to be described herein, the coating can also alter the morphology of the surface to enhance specific end uses. Open end 254a is sealed by a first sealing means while open end 254b is sealed by a second sealing means. The first sealing means comprises a hollow elastomeric plug 256 which is sealably received within end 254a of tubular member 254. Mounted internally of plug 256 is a valve member 258. Similarly, the second sealing means comprises a hollow elastomeric plug 258 having mounted therewithin a valve member 260. Both the proximal and distal ends of the adding means are sealed by frangible means shown in FIG. 19 as frangible disks 254f. These disks are adhesively bonded to the outboard surfaces of plugs 256 and 258 and are rupturable by the valve operators of the apparatus. Disks 254f can be constructed from any suitable frangible polymer.

Disposed internally of tubular member 254 is the additive carrying means of the invention here shown as a cylindrically shaped porous substrate or scaffold 265. As before, scaffold 265 is preferably a microporous, polymeric functional support of the character previously described to which various additives including beneficial agents such as drugs, biologically active materials, and chemical elements and compounds can be releasably connected. These additives are supported by the scaffold or substrate 265 in a manner such that as the liquid component contained within vial 230, such as a diluent, reagent, or aqueous solvent flows around, about and through the scaffold, the additives will be reacted, released, separated and intermixed with the liquid component.

Disposed proximate the first and second ends of tubular member 254 are first and second porous members 268 and 270 respectively. Member 268 is located between scaffold 265 and plug 256 and is provided with a central cavity 268a which is adapted to receive valve member 258 when the first valve means is open. Similarly, member 270 is located between scaffold 265 and plug 258 and is provided with a central cavity 270a which is adapted to receive valve member 260 when the second valve means is open. The plug and the porous members are secured within the ends of tubular member 254 by crimp caps 271, the inboard peripheries 271a of which are crimped into annular grooves 254c formed in member 254 (FIG. 20).

Following the removal of the sterile tear-off caps 269 from each end of the adding means subassembly, the subassembly is inserted into the first or open threaded end of the housing. Tab 271b (FIG. 19) of crimp cap 271 polarizes the subassembly for correct orientation. This done, threaded cap assembly 212 is connected to the housing. During this step, air contained within the cap interior is vented through vent aperture "V" (FIG. 20). Additionally, the previously identified first valve operating means opens the second valve means of the adding means subassembly by forcing valve member 260 into cavity 270a of porous member 270 (see FIG. 22). As best seen in FIG. 20, the first valve operating means comprises tubular housing 273 which is integrally formed with cap 222 and a tongue-like first valve operator 274 which is movable into engagement with the valve member as the cap is connected to the syringe housing As will also be observed by referring to FIGS. 22 and 23, as the adding means subassembly is inserted into the syringe housing, a second valve operating means moves the first valve means of the adding means subassembly into a valve open position. This second valve operating means comprises a part of a dual valve operator 277, the character of which is best seen in FIG. 24. Dual valve operator 277 comprises a partition wall 279 formed interiorly of wall 204 proximate end 204b thereof (FIG. 20). Extending inwardly of the syringe housing is the second valve operating means and extending outwardly, in the opposite direction, is the third valve operating means. Each of the second and third valve operating means comprises a tubular member 280 within which a tongue-like valve operator 282 is supported. The inwardly extending operator, identified as 282a engages valve member 258 as the adding means is inserted into the syringe housing and moves it into cavity 268a of porous member 268. As indicated in FIG. 23, this opens a fluid flow path toward scaffold 265. Because tubular member 280 is sealably received with the central passageway of elastomeric plug 256, leakage between member 280 and plug 256 is prevented.

With the adding means thusly positioned within the syringe housing, cap 222 is locked against removal by a plurality of locking tabs 222a which are provided on cap 222 and which lockably engage a plurality of cooperating tabs 204d provided on wall 204. Next, the plugged end of the fluid container assembly 208 is telescopically inserted into the open second end portion 204b of the syringe housing in the manner shown in FIG. 22 so that the wall of container 230 is telescopically received within channel 206. Inward pressure directed against the container subassembly will cause the valve operator designated as 282b to engage valve member 258 and move it into cavity 268a thereby moving the valve into the open position shown in FIGS. 22 and 23. This places the interior of container 230 in fluid communication with the internal chamber of tubular member 254 so that fluid contained within the container can flow inwardly into the inner chamber of the tubular member and then around, about and through scaffold 265. With the cannula closure cap 287 removed (FIGS. 18 and 20), the fluid mixture can flow outwardly of the device via passageway 220, 222a and 219 (FIG. 22). The exertion of a continued inward pressure against container 230 will cause the end cap 285 of the container assembly to move into close proximity with end 204b of the syringe housing and will result in locking means provided on the cap interlocking with the housing in the manner shown in FIG. 23. More particularly, the locking means, which here comprises a locking collar 285a, will be urged into locking engagement with a groove 205 provided in housing 202 thereby preventing removal of the container assembly from the syringe housing. Air contained within channel 206 will be vented to atmosphere via vent V-1 (FIG. 20).

Turning now to FIGS. 25 through 29, yet another form of the mixing and delivery syringe assembly of the present invention is there illustrated and generally identified by the numeral 300. This form of the invention is similar in many respects to the embodiment described in FIGS. 18 through 20, but includes piercing cannula means rather than valve means for controlling fluid flow into and out of the mixing chamber of the device. Like numerals are used to identify like components to those shown in FIGS. 18 through 20.

As best seen in FIGS. 25 through 28, the apparatus of this latest embodiment of the invention comprises a hollow housing 302 having an outer wall 304 provided with a longitudinally extending, circumferential channel 306 (FIG. 28). In a manner presently to be described, channel 306 closely receives the outer wall of the fluid container subassembly 308 of the apparatus as the fluid container is mated with the syringe housing. Connected to wall 304 and extending outwardly therefrom are oppositely disposed gripping elements 310, which are configured to receive the fingers of the user. The forward end 304a of wall 304 is threaded to threadably receive a closure cap assembly 312 within which is mounted a first piercing cannula means, the purpose and character of which will be described in the paragraphs which follow.

Integrally formed with cap assembly 312 and extending outwardly therefrom is a cannula assembly 214 which is of identical construction to that previously described and includes a blunt end cannula 217. Cannula 217 has an internal flow passageway 219 which is in communication with a fluid flow passageway 320 provided in the previously identified first piercing cannula means. As best seen in FIG. 25, cap portion 322 of cap assembly 312 is provided with a fluid passageway 322a which interconnects passageways 219 and 320.

The container means of this latest form of the invention is of slightly different construction and includes a piercable plug 329 rather than a valve means. The container means also comprises a container 330 which forms a part of container subassembly 308. Container 330 is adapted to contain a first fluid component such as a diluent or other parenteral fluid "F" and has a closed end 332 and an open end 334 within which plug 329 is sealably mounted. As before, open end 334 of the container is normally closed by a sterile tear off type cap similar to the previously described cap 136.

As best seen in FIG. 25, a plug 329 which is constructed of an elastomeric material such as soft rubber, is provided with an elongated central bore 329a that terminates at a thin wall section 329b. As before, plug 329 is telescopically movable within an internal chamber 339 of vial 330 between first and second positions. The outboard end of plug 329 is threaded to permit threaded interconnection with the syringe housing in a manner presently to be described.

As was the case with the earlier described embodiments, adding means is provided for adding a second component such as a drug or other beneficial agent to the first fluid component contained within vial 330. In the form of the invention shown in FIGS. 25 through 29, the adding means comprises an assembly made up of a tubular member 354 having first and second open ends 354a and 354b. Open end 354a is sealed by a first sealing means while open end 354b is sealed by a second sealing means. The first sealing means comprises an elastomeric plug 356 which is sealably received within end 354a of tubular member 354. Similarly, the second sealing means comprises a hollow elastomeric plug 358 sealably mounted within end 354b of a member 354.

Disposed internally of tubular member 354 is the additive carrying means of the invention here shown as a cylindrically shaped synthetic porous substrate or scaffold 365. As before, scaffold 365 is preferably a microporous, polymeric support constructed of a synthetic material to which various additives including beneficial agents such as drugs, biologically active materials, and chemical elements and compounds can be releasably connected. These additives are supported by the scaffold or substrate 365 in a manner such that as the liquid component contained within vial 330, such as a diluent, reagent, or aqueous solvent flows around, about and through the scaffold, the additives will be reacted, released, separated and intermixed with the liquid component.

As best seen in FIG. 25, both of the plug members 356 and 358 are provided with a central cavity 359 which terminates in a penetrable wall portion 361. Plugs 356 and 358 are secured within the ends of tubular member 354 by crimp caps 271, the inboard peripheries 271a of which are crimped into annular grooves 354c formed in member 354 (FIG. 25).

Following the removal of the sterile tear-off caps from each end of the adding means slab assembly, the subassembly is inserted into the open threaded end of the housing. This done, threaded cap assembly 312 is connected to the housing. During this step, the first piercing cannula 370 of the first piercing means pierces wall 361 of plug 358 of the adding means subassembly thereby opening fluid communication between passageways 320 and 21a of the blunt cannula 217.

As will also be observed by referring to FIGS. 25 and 28, as the adding means subassembly is inserted into the syringe housing, a second piercing cannula 372 of the second piercing means pierces end wall 361 of plug 356. This second piercing means comprises a part of a dual piercing means, the character of which is best seen in FIG. 25. The dual piercing means here comprises a partition wall 376 formed interiorly of wall 304. Extending inwardly of the syringe housing is the second piercing cannula 372 and extending outwardly, in the opposite direction, is the third piercing cannula 378 of the third piercing means. Each of the second and third piercing cannulas includes a fluid passageway. These passageways, 372a and 378a, are in communication with a central passageway 376a formed in partition wall 376 (FIG. 25). The piercing of plug 356 by cannula 372 opens a fluid flow path toward the scaffold of the adding means in the manner shown in FIG. 29.

With the adding means thusly positioned within the syringe housing, cap 322 is, as before, locked against removal by a plurality of locking tabs 322a which are provided on cap 322 and which lockably engage a plurality of cooperating tabs 204d provided on wall 304. Next, the plugged end of the fluid container assembly 308 is telescopically inserted into the open end 304b of the syringe housing in the manner shown in FIG. 28 so that the wall of container 330 is telescopically received within channel 306. Inward pressure directed against the container subassembly will cause the third piercing cannula 378 to pierce wall 329b of plug 329 thereby placing the interior of container 330 in fluid communication with the internal chamber of tubular member 354 so that fluid contained within the container can flow inwardly into the inner chamber of the tubular member and then around, about and through scaffold 365 (FIG. 29). With the cannula closure cap 287 removed (FIG. 25), the fluid mixture can flow outwardly of the device via passageway 320, 322a and 219 (FIG. 28).

Referring to FIG. 25A an alternate form of cannula is there shown. This cannula comprises a hollow needle type cannula 217a and is usable in lieu of blunt cannula 217.

The exertion of a continued inward pressure against container 330 will, as before, cause the end cap 285 of the container assembly to move into close proximity with end 304b of the syringe housing and will result in locking means provided on the cap, interlocking with the housing in the manner shown in FIG. 29. More particularly, threads 304t provided proximate end 304b of the syringe housing will be engaged by threads 329t provided on plug 329. Rotation of cap 285 will cause plug 329 to be threadably received within the syringe housing.

Turning now to FIGS. 26 and 27, it is to be noted that additional locking means are provided to interlock plug 329 with the syringe housing once the components have been mated. This additional locking means comprises a generally crescent shaped protuberance 383 formed on partition wall 376 and a cooperating, generally crescent shaped groove 385 formed in elastomeric plug 329 of the container assembly. When the parts are threadably mated in the manner shown in FIG. 29, protuberance 383 will enter groove 385. Upon continued rotational forces being applied to cap 285, protuberance 383 will lockably wedge within groove 385 thereby securely locking plug 329 to partition wall 376. System venting is accomplished via vents "V" and "V-1" in the manner previously described.

Referring to FIGS. 30 through 34, still another form of the mixing and delivery syringe assembly of the present invention is there illustrated and generally identified by the numeral 400. This last form of the invention is similar in many respects to the embodiment of the invention shown in FIGS. 13 and 18 through 21, but includes a fluid container, a syringe body, and an adding means, each of which is non-circular in cross section. Additionally, the adding means is of slightly different internal construction. The apparatus of this latest embodiment comprises a hollow housing 402 having an outer wall 404 provided with a longitudinally extending, circumferential channel 406 (FIG. 31). As best seen in FIG. 31, housing 402 is generally elliptical in cross section. Connected to wall 404 and extending outwardly therefrom are oppositely disposed gripping elements 410, which are configured to receive the fingers of the user. The forward or first end 404a, of wall 404 is generally cylindrical in shape and is threaded to threadably receive a closure cap assembly 412 which is also generally cylindrical in cross section. Mounted within cap assembly 412 is a first valve operating means, the purpose and character of which is identical to that previously described in connection with FIGS. 18 through 21. Attached to cap assembly 412 and extending outwardly therefrom is a cannula assembly 414 which is also identical to cannula assembly 214.

The container means of this latest form of the invention is valved in the same manner and operates in the same manner as the container means of FIG. 13 and comprises a container 430 which forms a part of container subassembly 408. Container 430 is generally elliptical is shape and adapted to contain a first fluid component such as a diluent or other parenteral fluid "F" and has a closed end 432 and an open end 434 within which the valve means is sealably mounted. Open end 434 of the container or vial 430 is normally closed by a sterile tear off type cap similar to the previously described cap 136. The valve means of the invention includes a plug 438 which is constructed of an elastomeric material such as soft rubber. The fluid outlet passageway of the valves is closed by frangible means shown here as a frangible disk 241 of the character previously described. As before, plug 438 is telescopically movable within an internal chamber 439 of vial 430 between first and second positions. Disposed internally of plug 438 is a valve assembly 440 for permitting the fluid "F" contained within the vial to flow outwardly thereof after the sterile closure cap has been removed from the vial assembly and following rupture of frangible disk 241. Valve assembly 440 is of identical construction and operation to valve assembly 240 and the details of its construction and operation will not be repeated.

A novel aspect of the container of this latest embodiment of the invention resides in the fact that the container 430 is formed of a plastic material and includes an inner surface which is provided with container barrier means here shown in the form of a surface modification coating 430a. The barrier container means lengthens product shelf life and functions as a vapor and gas transmission barrier, having, for example, improved resistance to oxygen permeability.

Coating 430a is a functional coating comprising a thin film having vapor barrier properties. In the preferred form, a silicon oxide based film is deposited and adheres to the interior interface of the plastic vial. Various base plastics such as poly (ethyleneterephthalate (PET) or polycarbonate (PC) can be employed as the vial substrate materials, and subsequently treated by the plasma deposition of silicon oxide.

Alternate forms of coating 430a include functional composite coatings of aluminium oxide and silicon dioxide, or multilayer films of plasma deposited Hydrogenated Amorphous silicon (a–s::H) and silicon nitride, and other layering of micro crystalline silicon (mu c–s1) deposition.

As was the case with the earlier described embodiments, adding means is provided for adding a second component such as a drug or other beneficial agent to the first fluid component contained within vial 430. In the form of the invention shown in FIGS. 30 through 34, the adding means comprises an assembly made up of a tubular member 454 having first and second open ends 454a and 454b. As before, 454a is sealed by a first sealing means while open end 454b is sealed by a second sealing means. The sealing means are as previously described in connection with FIGS. 18 through 21.

Disposed internally of tubular member 454 is the additive carrying means of the invention, here shown as a generally elliptically shaped porous substrate or scaffold 465 (FIG. 32). As before, scaffold 465 is preferably a synthetic microporous, polymeric support of the character previously described to which various additives including beneficial agents such as drugs, biologically active materials, and chemical elements and compounds can be releasably connected. These additives are supported by the scaffold or substrate 465 in a manner such that as the liquid component contained within vial 430, such as a diluent, reagent, or aqueous solvent flows around, about and through the scaffold, the additives will be reacted, released, separated and intermixed with the liquid component.

As best seen in FIG. 32, which is a cross-sectional view of assembly 454, the substrate is maintained in a spaced relationship with inner wall 454i of tubular member 454 by circumferentially spaced offsets 455. With this construction, fluid flow around and about the scaffold is enhanced.

Tubular member 454 can be a glass vial, or a plastic vial, the interior of which is covered by vial barrier means, here comprising thin laminate coating 457i (FIG. 32A) which comprise first and second layers 457i-1 and 457i-2. These layers cooperate to form a tailored barrier structure which alters the surface morphology of the vial, its functional characteristics, including the reactivity of the surface, and which can control the diffusion transport of water, water vapor and various gases. The materials used to form the layers can selectively comprise both rubber and glassy advance polymers, including thermoplastic films such as polyvinylchloride (PVC), copolymers of vinylidene chloride and vinylchloride, polyethylene terephthalate (PET), tetrafluoroethylenehexafluoropropylene and vinylidene flouride (THV fluoroplastic) ethylene, vinyl alcohol copolymers, advance polyesters, such as polyethylene napthalene dicarboxylate, advance amorphous polymers, including polyvinyl chloride and polystyrene. The layers can also be formed in a manner well understood by those skilled in the art, of plasma deposited silicon oxide silicon dioxide, silicon nitride, alumium oxide and silicon dioxide and various like materials. Further, the layers can be formed through the evaporation of silicon monoxide, aluminum and magnesium in oxidizing atmospheres in accordance with well known prior art techniques.

When vial 454 is constructed of plastic, various oxygen barrier resins can also be used, including vinylidene chloride, aromatic nylon, amorphous nylon, polyacrylonitrile, polyacrylicimide and similar resins offered for sale by The Dow Chemical Company, Rohm & Hass and DuPont.

The vial barrier means can also function to provide a compatibility surface. Materials suitable for the formation of this compatibility surface comprise the previously identified plasma deposited surface modification materials as well as such other unique polymers, including poly-para-xylylene and other members of a unique polymer series, offered by various companies including Union Carbide under the name and style "Paralene".

Surface coatings of the character here contemplated can include single or multiple layers of similar or different materials. The interfacial coating or coatings can be employed to increase the functional surface compatibility of the vial base material with the intended vial contents, the barrier properties of the vial base materials, including its gas permeation, migration and perm select characteristics and for optimizing the morphology of the internal vial material for specific applications.

Materials suitable for the construction of plastic vials include polycarbonate, high and low density polyethylene, polypropylene, nylon, polystyrene, polyamides, styrenes, PET, and various like materials.

The exterior surface of vial 454 can also be provided with a negative permeation barrier means for preventing external migration of a penetrant into the interior of the vial. The negative permeation barrier means is shown in FIG. 32A as comprising a coating 457o. Coating 457o can comprise the same material, in the same configuration and applied in the same manner as used in connection with coating 457i as previously described herein.

Following the removal of the sterile tear-off caps from each end of the adding means subassembly, the subassembly is inserted into the first or open threaded end of the syringe housing and mixing is accomplished in the same manner as previously described in connection with the embodiment shown in FIGS. 18 through 21.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim

1. A device for intermixing a first component with a second component and for dispensing the mixture from the device comprising:
   (a) a housing having first and second end portions, and an internal chamber with an outlet;
   (b) container means connected to said second end portion of said housing containing a first component, said container means being movable relative to said chamber from a first position to a second position;
   (c) adding means disposed within said internal chamber for adding a second component to said first component to form an infusible mixture upon movement of said container means toward said second position, said adding means comprising a scaffold upon which said second component is removably carried in a manner such that said second component will be presented to said first component for removal thereby from said scaffold upon movement of said container means toward said second position;
   (d) valve means for controlling the flow of said first component from said container means toward said adding means; and
   (e) flow means for permitting fluid flow between said adding means and said outlet of said internal chamber upon movement of said container means toward said second position.

2. As device as defined in claim 1 in which said valve means comprises:
   (a) a valve housing including a valve seat disposed within said container means; and
   (b) a valve member movable relative to said valve seat between a valve closed and a valve open position.

3. A device as defined in claim 2 in which said adding means further comprises a vial having an internal chamber for containing said scaffold.

4. A device as defined in claim 3 further including valve operating means for moving said valve member between said valve closed and said valve open position.

5. A device as defined in claim 3 in which said scaffold comprises a microporous member having a microstructure of interconnecting voids, said second component extending into said voids.

6. A device as defined in claim 3 in which said first component comprises a parenteral liquid.

7. A device as defined in claim 6 in which said second component comprises a beneficial agent.

8. A device for intermixing a first component with a second component to form an infusible mixture and for dispensing the infusible mixture from the device into the environment of use, said device comprising:
   (a) a hollow housing having an internal chamber and first and second ends;
   (b) a closure cap connected to said first end of said hollow housing, said cap having a passageway in communication with said internal chamber of said hollow housing;
   (c) container means connected to said second end of said hollow housing for telescopic movement relative said internal chamber from a first position to a second position, a container means containing said first component;
   (d) adding means removably receivable within said internal chamber of said hollow housing for adding a second component to said first component to form an infusible mixture upon movement of said container means toward said second position, said adding means comprising a scaffold upon which said second component is removably affixed so that said second component will be presented to said first component for removal from said scaffold upon movement of said container means relative to said internal chamber;
   (e) first means for controlling the passage of said first component toward said adding means; and
   (f) second means for controlling the passage of said infusible mixture between said adding means and said passage of said closure cap upon movement of said container means toward said second position.

9. A device as defined in claim 8 in which said first means comprises valve means disposed within said container means for controlling the passage of said first component toward said adding means.

10. A device as defined in claim 8 in which said first means comprises a piercing cannula connected to said housing proximate said second end thereof.

11. A device as defined in claim 8 in which said adding means includes a vial having a chamber and in which said second means comprises:
    (a) an outlet valve means disposed within said vial; and
    (b) a valve operating means disposed within said cap for operating said outlet valve means.

12. A device as defined in claim 8 in which said second means comprises a piercing cannula disposed within said cap.

13. A device as defined in claim 8 further including a blunt cannula connected to said closure cap.

14. A device as defined in claim 8 further including a needle type infusion cannula connected to said closure cap.

15. A device as defined in claim 8 in which said adding means comprises:
    (a) a vial having first and second ends and a chamber disposed therebetween, said scaffold being disposed within said chamber; and (b) first and second valves disposed within said first and second ends of said vial, respectively, for controlling the passage of said first component into said chamber and for controlling the passage of said infusible mixture out of said chamber.

16. A device as defined in claim 8 in which said adding means comprises:
   (a) a vial having first and second ends and a chamber disposed therebetween, said scaffold being disposed within said chamber; and
   (b) first and second penetrable plugs sealably connected to said vial proximate said first and second ends to seal said chamber relative to atmosphere.

17. A device as defined in claim 16 in which said first means comprises a penetrable plug sealably connected to said container.

18. A device as defined in claim 17 in which said hollow housing further includes a first piercing cannula protruding into said internal chamber of said housing and a second axially aligned piercing cannula extending oppositely with respect to said first piercing cannula.

19. A device as defined in claim 18 in which said hollow housing is threaded and in which said penetrable plug is provided with threads engageable with said threads of said hollow housing.

20. A device for intermixing a first component with a second component to form an infusible mixture and for dispensing the infusible mixture from the device into the environment of use, said device comprising:
   (a) a hollow housing having an internal chamber and first and second ends;
   (b) a closure cap connected to said first end of said hollow housing, said cap having a passageway in communication with said internal chamber of said hollow housing;
   (c) container means connected to said second end of said hollow housing for telescopic movement relative said internal chamber from a first position to a second position, said container means containing a first component;
   (d) adding means removably receivable within said internal chamber of said hollow housing for adding a second component to said first component to form infusible mixture upon movement of said container means toward said second position, said adding means comprising a vial having a chamber and a scaffold disposed within said chamber said second component being removably affixed to said scaffold for removal therefrom as said first component flows proximate said scaffold due to movement of said container means toward said second position;
   (e) first means for controlling the passage of said first component toward said adding means said first means comprising valve means disposed within said container for controlling the passage of said first component toward said adding means; and
   (f) second means for controlling the passage of said infusible mixture between said adding means and said passage of said closure cap upon movement of said container means toward said second position, said second means comprising:
       (i) an outlet valve means disposed within said vial; and
       (ii) a valve operating means disposed within said cap for operating said outlet valve means.

21. A device as defined in claim 20 in which said container means comprises a container having an internal wall and in which said container means further includes container barrier means disposed on said internal wall for providing a barrier to the passage of vapor and gas.

22. A device as defined in claim 20 in which said vial of said adding means has an external surface and in which said adding means further includes a negative permeation barrier means provided on said exterior surface of said vial for preventing permeation of external penetrants.

23. A device as defined in claim 20 in which said vial of said adding means has an interior surface and in which said adding means further includes vial barrier means provided on said interior surface of said vial for controlling the transport of water, water vapor and various gases.

24. A device as defined in claim 23 in which said vial barrier means provides a compatibility surface to ensure compatibility between said vial and fluid entering said chamber of said vial.

25. A device for intermixing a first component with a second component to form an infusible mixture and for dispensing the infusible mixture from the device into the environment of use, said device comprising:
   (a) a hollow housing having an internal chamber and first and second ends;
   (b) a closure cap connected to said first end of said hollow housing, said cap having a passageway in communication with said internal chamber of said hollow housing;
   (c) container means connected to said second end of said hollow housing for telescopic movement relative said internal chamber from a first position to a second position, said container means comprising a container having an internal wall, containing said first component, said container means further comprising container barrier means formed on said internal wall for providing a barrier to the passage of gases;
   (d) adding means removably receivable within said internal chamber of said hollow housing for adding a second component to said first component to form an infusible mixture upon movement of said container means toward said second position, said adding means comprising a vial having an external wall and an internal wall defining a chamber and a scaffold disposed within said chamber upon which said second component is removably affixed, for removal therefrom as said first component flows proximate said scaffold due to movement of said container means toward said second position said adding means further including vial barrier means formed on said internal wall for controlling the transport of water and gases;
   (e) first means for controlling the passage of said first component toward said adding means; and
   (f) second means for controlling the passage of said infusible mixture between said adding means and said passage of said closure cap upon movement of said container means toward said second position.

26. A device as defined in claim 25 in which said container barrier means comprises a silicon based film.

27. A device as defined in claim 25 in which said vial barrier means comprises a plurality of layers of materials.

28. A device as defined in claim 25 in which said vial barrier means comprises glassy polymers.

29. A device as defined in claim 25 in which said vial barrier means includes a film comprising poly-para-xylylene.

30. A device as defined in claim 25 further including negative permeation barrier means formed on said external surface of said vial of said adding means for preventing permeation of penetrants into said chamber of said vial.

31. A device as defined in claim 25 in which said first means comprises flow control means for controlling the rate of fluid flow toward said adding means.

32. A device as defined in claim 25 in which said second means comprises filter means for filtering said infusible mixture.

33. A device as defined in claim 25 in which said adding means includes an additive and in which second means comprises means for accomplishing secondary mixing of said fluid and said additive of said adding means.

34. A device as defined in claim 25 in which said second means comprises filter means for controlling the residence time of said first component within said chamber of said vial.

35. A device as defined in claim 25 in which said first means includes frangible means disposed between said adding means and said container means for substantially blocking passage of said first component toward said adding means.

36. A device as defined in claim 35 in which said frangible means comprises a frangible disk affixed to said container means.

37. A device as defined in claim 35 in which said frangible means comprises a frangible disk affixed to said adding means.

38. A device as defined in claim 35 in which said second means further includes frangible means for substantially blocking passage of said infusible mixture toward said passage of said closure cap.

* * * * *